US005695124A

United States Patent [19]

Demeny et al.

[11] Patent Number: 5,695,124

[45] Date of Patent: Dec. 9, 1997

[54] SELF-CONTAINED EMERGENCY EYE WASH STATION

[75] Inventors: Rodney L. Demeny, Medinah; Robert B. Hurley, Inverness; Richard J. Riback, Deerfield, all of Ill.

[73] Assignee: Fendall Company, Arlington Heights, Ill.

[21] Appl. No.: 655,764

[22] Filed: May 30, 1996

Related U.S. Application Data

[62] Division of Ser. No. 451,191, May 26, 1995, Pat. No. 5,566,406.

[51] Int. Cl.[6] .......... A61M 35/00; B05B 9/00; B65D 1/32; B65D 35/56

[52] U.S. Cl. .......... 239/327; 239/379; 239/562; 4/620; 222/105; 604/294; 604/295; 604/296

[58] Field of Search .......... 239/302, 328, 239/375, 376, 378, 379, 327, 557, 562, DIG. 12, 548; 4/620; 604/294, 295, 296; 222/105, 183, 330, 565, 527, 529, 485

[56] References Cited

U.S. PATENT DOCUMENTS

| | | | |
|---|---|---|---|
| 289,528 | 12/1883 | Goodner | 239/327 |
| 396,708 | 1/1889 | Payne . | |
| 1,759,459 | 5/1930 | Murdock . | |
| 3,261,355 | 7/1966 | Burbig | 604/296 |
| 3,871,554 | 3/1975 | Huck | 222/96 |
| 3,963,147 | 6/1976 | Waters . | |
| 4,012,798 | 3/1977 | Liautaud . | |
| 4,131,115 | 12/1978 | Peng | 128/249 |
| 4,278,089 | 7/1981 | Huck et al. | 128/278 |

(List continued on next page.)

FOREIGN PATENT DOCUMENTS

| | | | |
|---|---|---|---|
| 1281309 | 5/1962 | France . |
| 80792 | 9/1963 | France . |
| 2744545 | 4/1979 | Germany . |
| 2172934 | 10/1996 | United Kingdom . |

OTHER PUBLICATIONS

Emergency Eyewash Handbook, Fendall Company, Arlington Heights, Illinois, 1991, pp. 25–33.
Eyesaline Emergency Eye Wash Devices, Fendall Company, Arlington Heights, Illinois, Rev. Mar. 1992.
Porta Stream II with Eyesaline, Installation and Operation Manual, Fendall Company, Arlington Heighs, Illinois.
Zee—Your Total Eye Care Resource, Zee Medical, Inc., Irvine, California, Apr. 1989.
Specify Speakman Gravityflo™ Gravity Fed Eye/Face Wash, Speakman Company, Wilmington, Delaware, 1991.
Western Emergency Equipment Catalog Pages, Models W637, W660, and WP600, Western Emergency Equipment Emeryville, California, 1990, pp. 15–16.
ENCON Gravity Fed Portable Eyewash, Encon Safety Products, Houston, Texas.
Introducing KleerSight™, Bradley Corporation, Menomonee Falls, Wisconsin.
Speakman Emergency Equipment, Speakman Company, Wilmington, Delaware, 1993, pp. 10–23.

*Primary Examiner*—Andres Kashnikow
*Assistant Examiner*—Robin O. Evans
*Attorney, Agent, or Firm*—Arnold, White & Durkee

[57] ABSTRACT

A self-contained emergency eye wash station for dispensing eye wash fluid contained in a flexible container comprises a housing, a reservoir, and a platen. The housing supports the flexible container and supports a nozzle in fluid communication with the flexible container. The nozzle dispenses the eye wash fluid from the flexible container. The housing includes a drain capturing the eye wash fluid dispensed from the nozzle. The reservoir collects the eye wash fluid captured by the drain, and the reservoir is slidably mounted to the housing. The platen is connected to the reservoir. The platen is slidably movable relative to the housing and is located immediately above the flexible container. The platen presses downward on the flexible container with a downward force proportional to a weight of the eye wash fluid collected in the reservoir. The transfer of the weight of the eye wash fluid collected in the reservoir to the platen maintains a constant flow of eye wash fluid dispensed from the nozzle.

12 Claims, 19 Drawing Sheets

U.S. PATENT DOCUMENTS 4,363,146 12/1982 Liautaud .
4,632,276 12/1986 Makino .................................... 222/80
4,784,652 11/1988 Wikstrom ................................ 604/295
4,798,599 1/1989 Thomas .................................. 604/290
4,857,055 8/1989 Wang .
4,881,283 11/1989 Liautaud .................................... 4/620
4,939,800 7/1990 Fiorentino et al. ......................... 4/620
4,991,742 2/1991 Chang .
5,030,214 7/1991 Spector .................................. 604/301
5,269,445 12/1993 Tobler ................................ 239/327 X
5,346,132 9/1994 Hahn et al. ............................... 839/71
5,381,567 1/1995 Tanner et al. .
5,607,410 3/1997 Branch .................................. 604/302

SELF-CONTAINED EMERGENCY EYE WASH STATION

This is a divisional of application Ser. No. 08/451,191, filed May 26, 1995 now U.S. Pat. No. 5,566,406.

FIELD OF THE INVENTION

The present invention generally relates to self-contained emergency eye wash stations. More particularly, the present invention relates to an emergency eye wash station which employs a unique feedback mechanism for maintaining a constant flow of eye wash fluid upon actuation of the eye wash station and which employs a self-contained delivery system for maintaining long-term stability of the eye wash fluid prior to actuation of the eye wash station.

BACKGROUND OF THE INVENTION

Government and employers are increasingly aware of the need for protecting the health and safety of workers. For this reason, it is common to find eye wash fountains at industrial work stations, laboratories, and other locations where workers are exposed to gaseous fumes, liquids or solid materials which can irritate or injure eyes upon contact therewith. The Occupational Safety and Health Administration (OSHA) has made eye wash fountains mandatory for particular industrial work stations.

Some prior art devices have employed eye wash fountains providing sprays of water from regular plant plumbing connections. Other prior art devices, such as the eye wash fountains disclosed in U.S. Pat. No. 4,012,798 to Liautaud and U.S. Pat. No. 4,363,146 to Liautaud, are self-contained, gravity-fed, and independent of any plumbing connections. Such eye wash fountains typically contain a reservoir (or bottle) of wash fluid spaced above two opposed liquid spray nozzles. Upon activating the fluid flow, the wash fluid from the reservoir is fed solely by gravity to the nozzles to cause a gravity-induced spray of wash fluid from the nozzles.

In an effort to encourage suitable eye wash facilities, the American National Standards Institute (ANSI) has promulgated voluntary standards for portable eye wash fountains relating to flushing periods and the rate of flow of wash fluid. These standards dictate that portable eye wash fountains should deliver no less than 0.4 gallons per minute (1.5 liters per minute) of eye wash fluid for a time period of 15 minutes.

A drawback of the gravity-fed eye wash fountains of the type described above is that they contain fluid significantly in excess of the amount required for actual flushing to meet the ANSI standards because the rate of flow of wash fluid from the gravity-fed eye wash fountains decreases over time. The reason for this decrease in fluid flow rate over time is that the fluid head height in the reservoir decreases as the wash fluid is dispensed from the nozzles, thereby decreasing the amount of hydraulic pressure on the wash fluid over time. This reduction in hydraulic pressure over time causes a corresponding decrease in the fluid flow rate. To provide 0.4 gallons per minute of wash fluid for a full 15 minutes, the reservoirs of gravity-fed eye wash fountains must hold a sufficient amount of eye wash fluid that the fluid flow rate does not drop below 0.4 gallons per minute prior to 15 minutes from activation.

Another drawback of the gravity-fed portable eye wash fountains is that the rate of flow of wash fluid is not constant, but rather changes over time. The fluid flow rate is initially quite high so that the fluid flow rate does not drop below 0.4 gallons per minute after 15 minutes. The changes in fluid flow rate can limit effective flushing.

A further drawback of gravity-fed portable eye wash fountains is they often waste much of the wash fluid in the reservoir (as much as 30 percent of the initial supply) because there is insufficient hydraulic pressure to force all of the wash fluid from the reservoir through the nozzles. The flow of wash fluid through the nozzles substantially stops after only a portion of the wash fluid in the reservoir has been dispensed from the nozzles.

Yet another drawback of existing eye wash fountains is that they do not maintain the stability of the wash fluid in the reservoir for extended periods of time and, as a result, the wash fluid must be replaced with fresh wash fluid at fairly short time intervals. The fluid delivery systems of existing eye wash fountains generally require some exposure of the wash fluid in the reservoir to air. This exposure to air improves the flow of the wash fluid through the nozzles. At the same time, the exposure to air encourages the growth of bacteria existing in the wash fluid and the eye wash fountains themselves. The wash fluid in these eye wash fountains is stagnant, and at ambient temperature the environment is conducive to the growth of micro-organism populations. With this growth of bacteria, the wash fluid typically must be replaced with fresh wash fluid at least every six months, even when treated with preservatives. Further, most existing eye wash fountains employ tap water which contains chemical and solid particle contaminants such as chlorine, lead, and rust. The replacement of wash fluid is time-consuming and expensive in terms of both labor and materials.

Yet a further drawback of existing eye wash fountains is that the wash fluid dispensed from the nozzles generally is drained onto the floor, resulting in a mess which must be cleaned up. Alternatively, the used eye wash fluid is drained into an extra floor-standing container separate from the eye wash fountain. The extra container, in combination with the eye wash fountain, occupies a large amount of space.

An additional drawback of existing eye wash fountains is that the eye wash fountains typically must be removed from their operating position for draining of unused wash fluid, cleaning, and refilling with fresh wash fluid. Such removal of the eye wash fountains from their operating position is burdensome and time-consuming. When refilled and ready to be returned to their operating position, the units often weigh in excess of 130 pounds.

A need therefore exists for a self-contained eye wash station which overcomes the aforementioned shortcomings associated with existing portable eye wash fountains.

SUMMARY OF THE INVENTION

In one aspect of the present invention, a self-contained emergency eye wash station for dispensing eye wash fluid contained in a flexible container comprises a housing, a reservoir, and a platen. The housing supports the flexible container and supports a nozzle in fluid communication with the flexible container. The nozzle dispenses the eye wash fluid from the flexible container. The housing includes a drain capturing the eye wash fluid dispensed from the nozzle. The reservoir collects the eye wash fluid captured by the drain, and the reservoir is slidably mounted to the housing. The platen is connected to the reservoir. The platen is slidably movable relative to the housing and is located immediately above the flexible container. The platen presses downward on the flexible container with a downward force proportional to a weight of the eye wash fluid collected in the reservoir. The transfer of the weight of the eye wash fluid collected in the reservoir to the platen maintains a constant flow of eye wash fluid dispensed from the nozzle.

In another aspect of the present invention, the emergency eye wash station employs a self-contained delivery system comprising a flexible container containing an eye wash fluid, a nozzle, a seal element, and an actuation element. The nozzle is in fluid communication with the container and is detachably connectable to a housing of the eye wash station. The nozzle includes an upper pressure plate and a lower nozzle body. The lower nozzle body forms an inlet for receiving the eye wash fluid from the container and forms a plurality of apertures in fluid communication with the inlet. The upper pressure plate is detachably linked to the lower nozzle body. The seal element is removably coupled to the nozzle. The seal element firmly secures the upper pressure plate to the lower nozzle body such that the upper pressure plate blocks the apertures formed in the lower nozzle body. The actuation element is coupled to the seal element. The self-contained delivery system is able to maintain long-term stability of the eye wash fluid.

BRIEF DESCRIPTION OF THE DRAWINGS

Other objects and advantages of the present invention will become apparent upon reading the following detailed description and upon reference to the accompanying drawings, in which.

Figure 1:
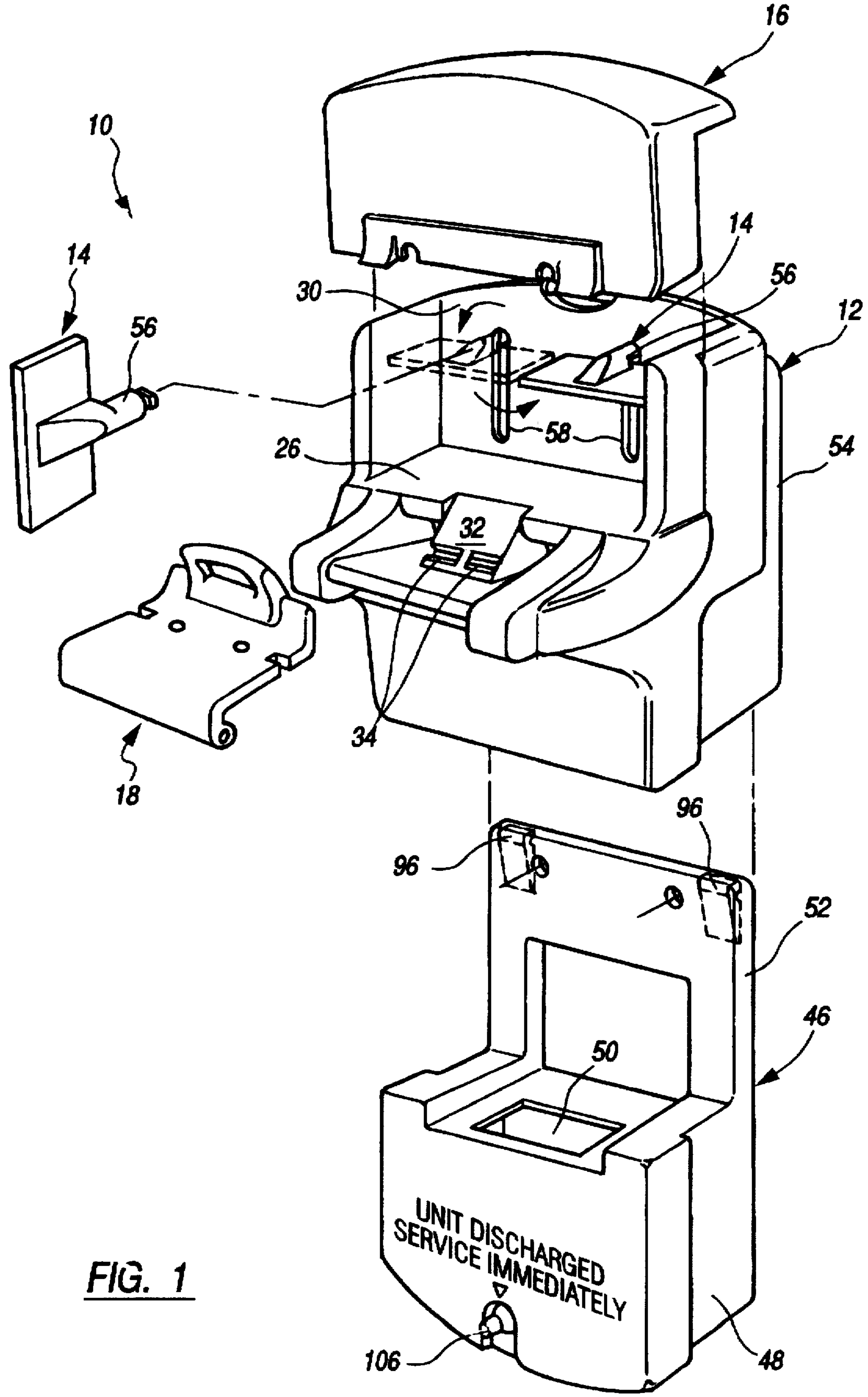
FIG. 1 is an exploded perspective view of a self-contained emergency eye wash station embodying the present invention, showing the eye wash station without an eye wash fluid delivery system loaded therein.

While the invention is susceptible to various modifications and alternative forms, a specific embodiment thereof has been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

DESCRIPTION OF THE PREFERRED EMBODIMENT

Figure 2:
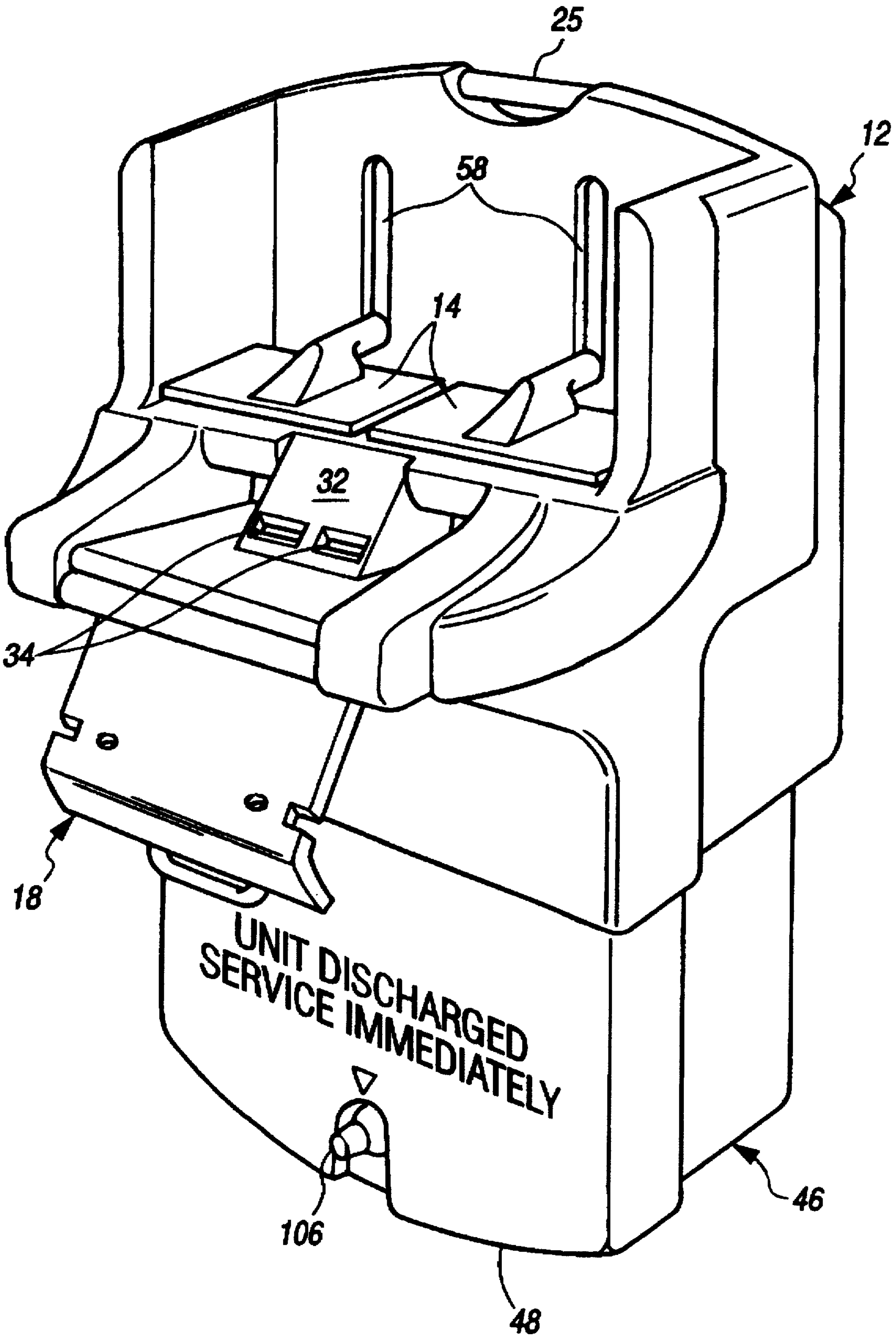
FIG. 2 is a perspective view of the eye wash station without the cover mounted thereto, with an actuation door pivotally mounted thereto in an open position, without an eye wash fluid delivery system loaded therein, and with platens disposed in a lower position.
Figure 3:
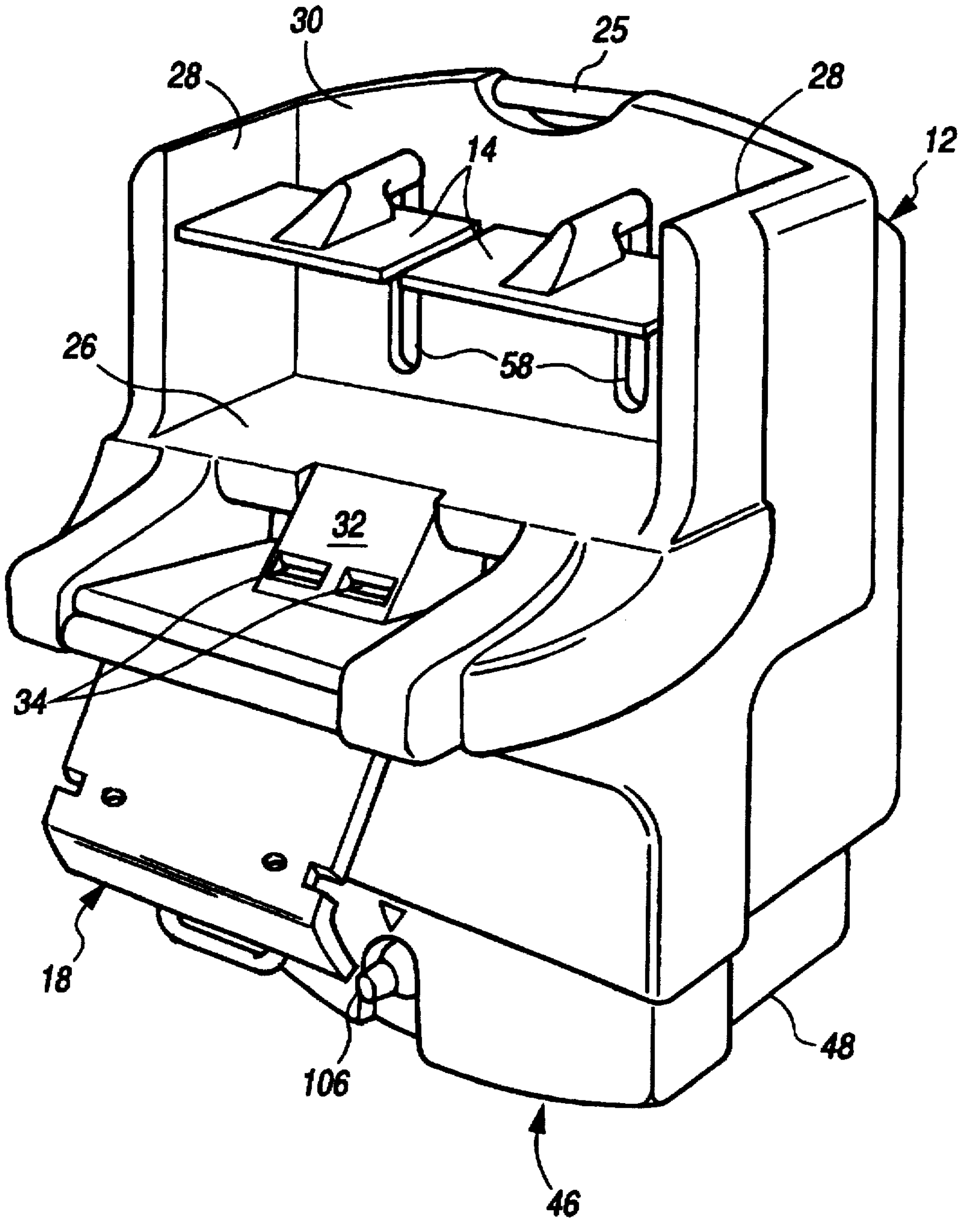
FIG. 3 is a perspective view of the eye wash station without the cover mounted thereto, with the actuation door pivotally mounted thereto in the open position, without the fluid delivery system loaded therein, and with the platens disposed in an upper position.
Figure 4:
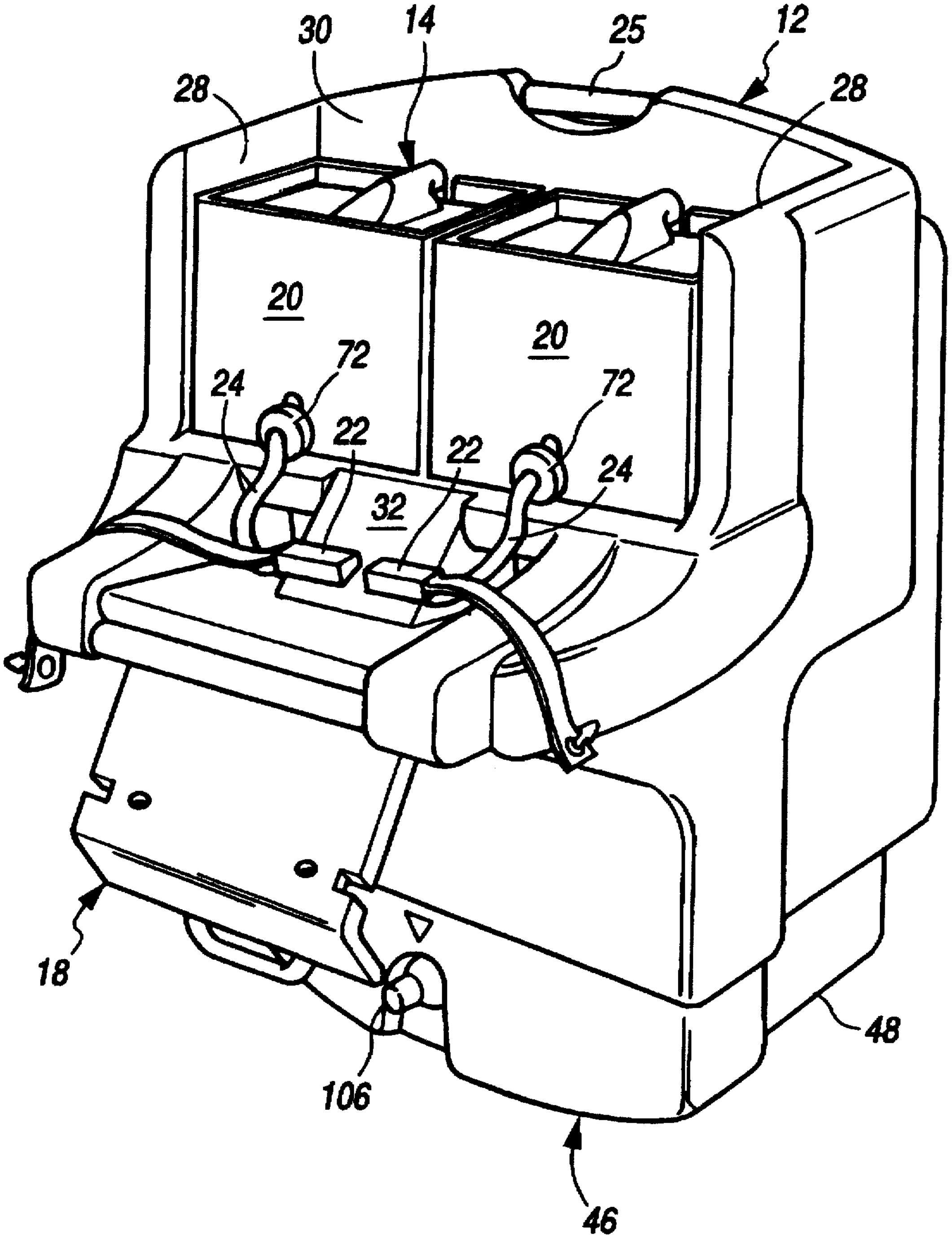
FIG. 4 is a perspective view of the eye wash station without the cover mounted thereto, with the actuation door pivotally mounted thereto in the open position, and with the fluid delivery system loaded therein.
Figure 5:
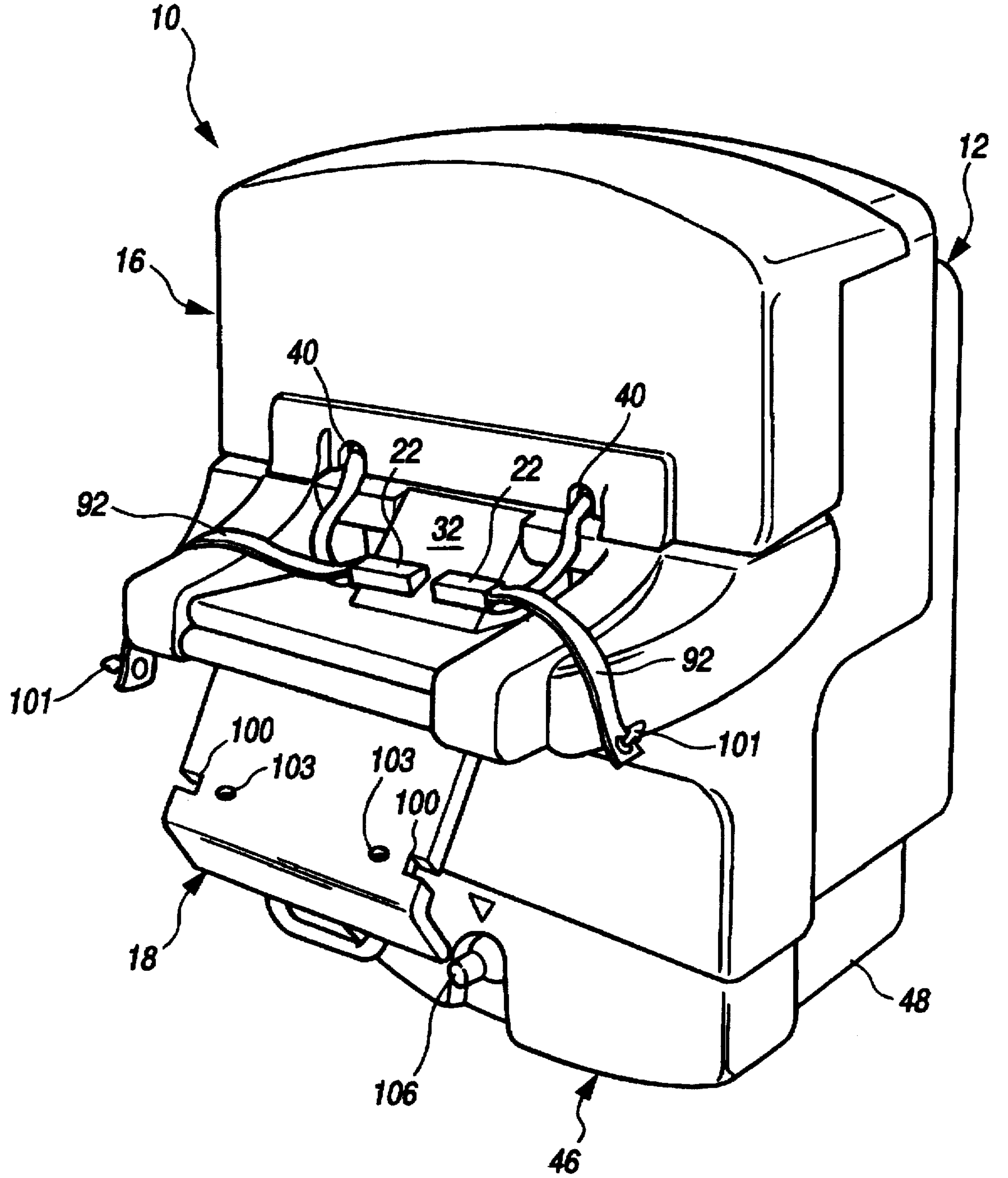
FIG. 5 is a perspective view of the eye wash station with the cover slidably mounted thereto in a closed position, with the actuation door pivotally mounted thereto in the open position, and with the fluid delivery system loaded therein.
Figure 6:
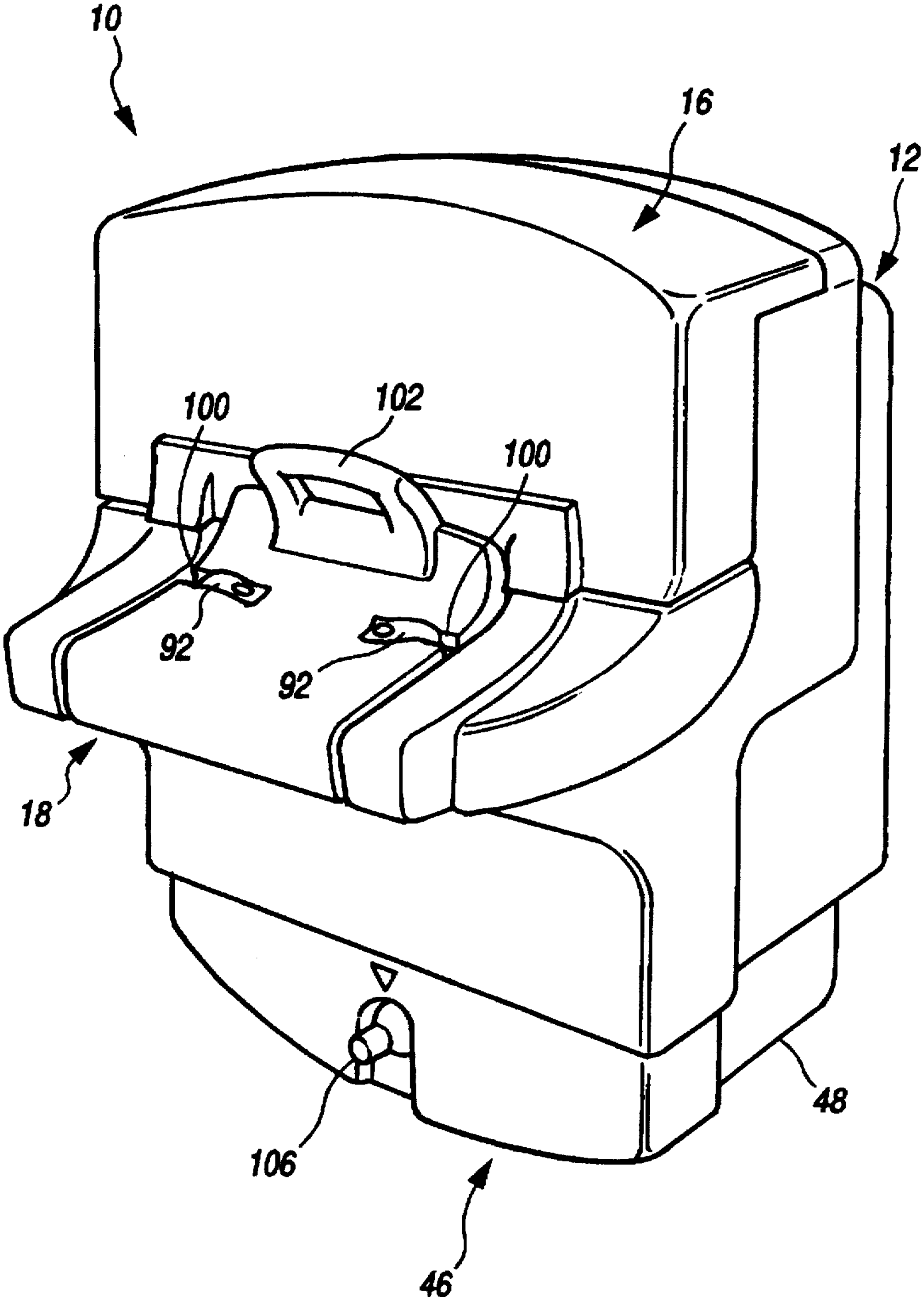
FIG. 6 is a perspective view of the eye wash station with the cover slidably mounted thereto in the closed position, with the actuation door pivotally mounted thereto in a closed position, and with the fluid delivery system loaded therein.
Figure 7:
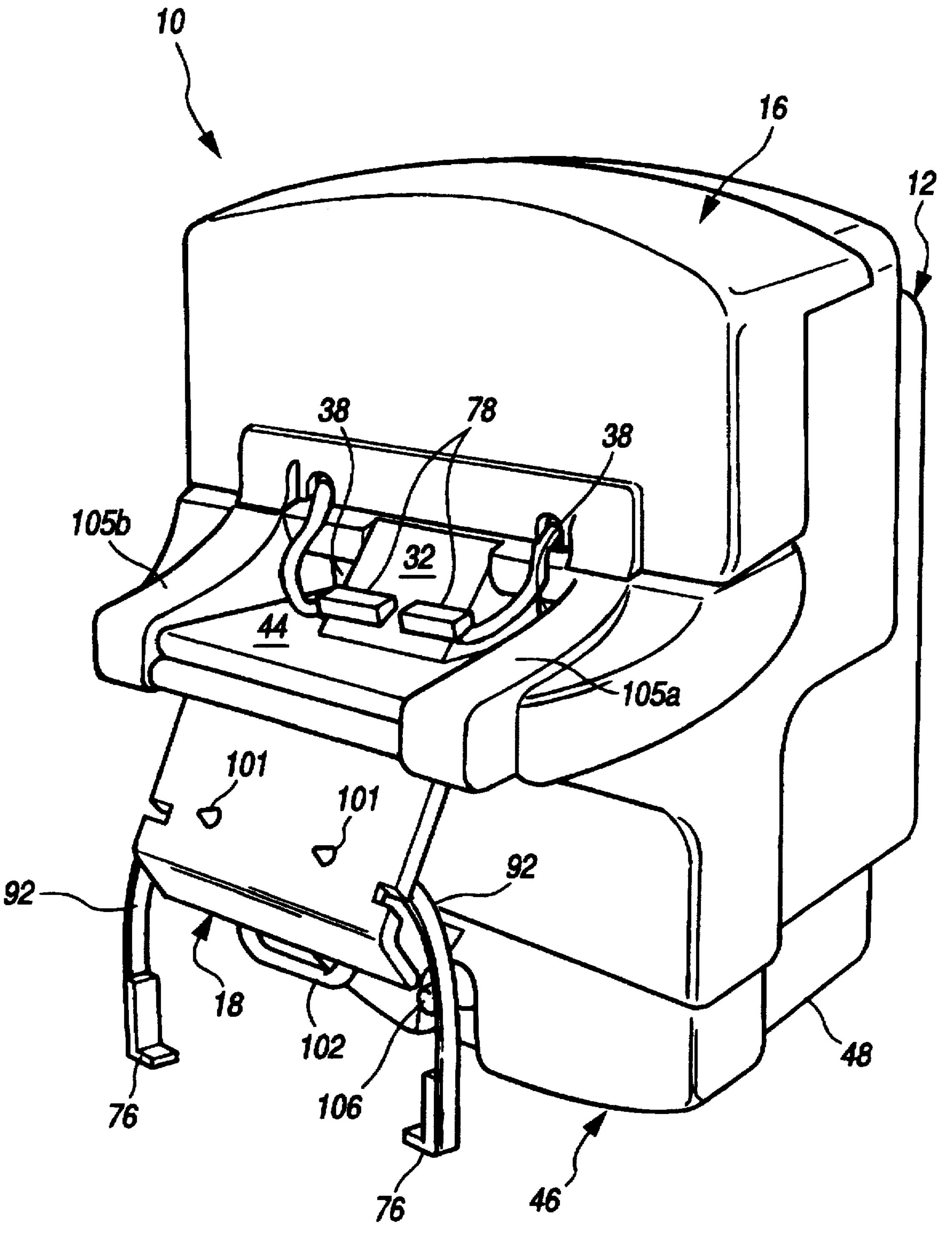
FIG. 7 is a perspective view of the eye wash station with the cover slidably mounted thereto in the closed position and with the actuation door rotated to the open position to initiate fluid flow from nozzles of the station.
Figure 18:
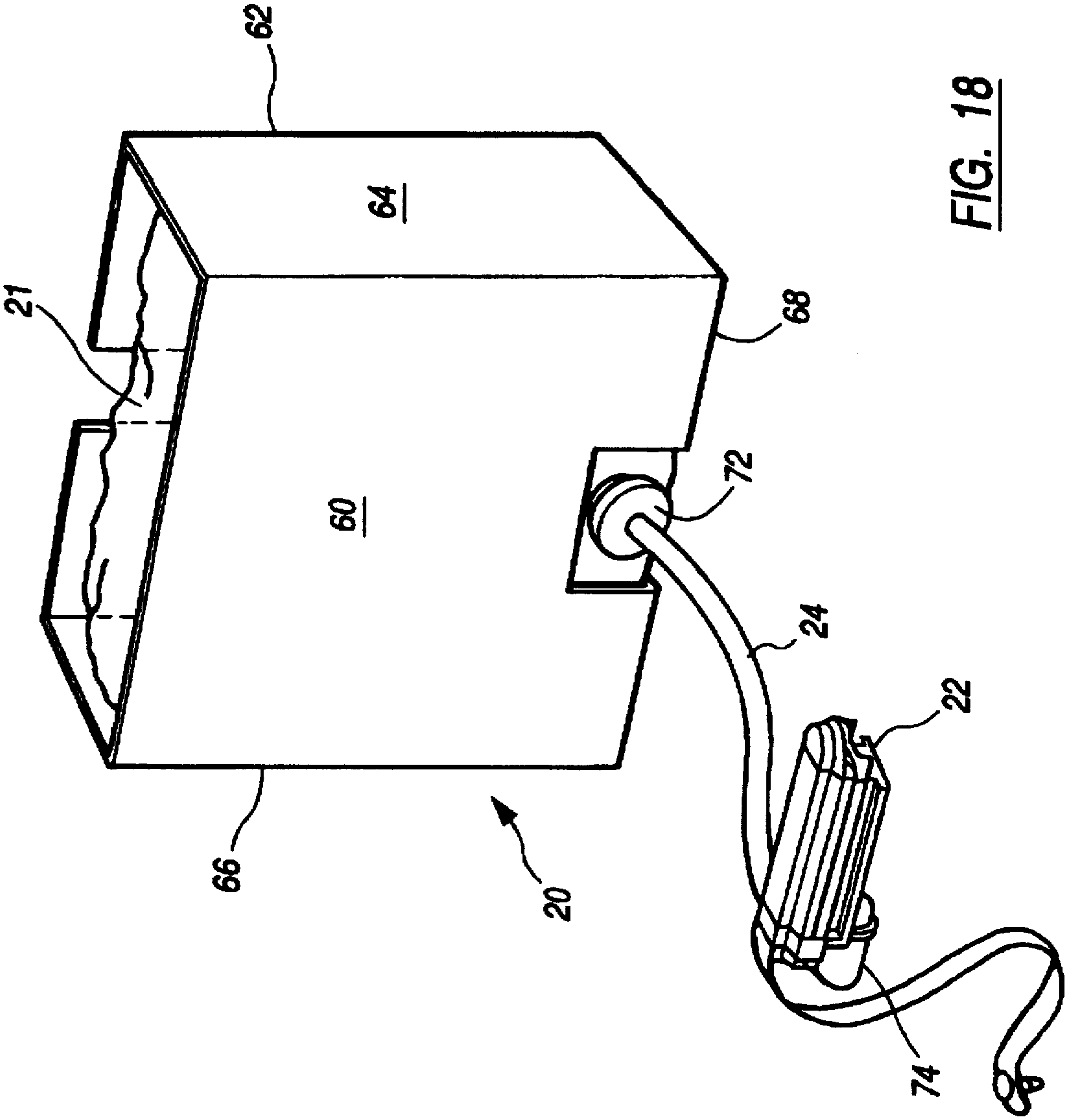
FIG. 18 is a perspective view of a self-contained fluid delivery system of the eye wash station in accordance with the present invention.

Turning now to the drawings, FIGS. 1–7 illustrate a self-contained emergency eye wash station 10 used to dispense eye wash fluid contained in a pair of flexible containers. FIG. 1 is an exploded view depicting various components of the eye wash station 10, including a housing 12, a pair of platens 14, a cover 16, an actuation door 18, and a reservoir 46. In addition to the foregoing components, the eye wash station 10 includes a self-contained eye wash fluid delivery system having a pair of identical delivery arrangements. One of these delivery arrangements is best shown in FIG. 18 prior to installation in the housing 12. The delivery arrangement in FIG. 18 includes a box 20, a flexible container 21 holding eye wash fluid, a nozzle 22, and a hose 24. FIGS. 2–6 illustrate the sequence of preparing the eye wash station 10 for use, and FIG. 7 illustrates the eye wash station 10 after it has been activated. Briefly, in this sequence of preparing the eye wash station 10 for use, the platens 14 are raised from a lower position in FIG. 2 to an upper position in FIG. 3. The platens 14 are temporarily locked in this upper position using a latching mechanism described in detail below. With the platens 14 locked in the upper position, the fluid delivery system is loaded into the housing 12 as shown in FIG. 4. Next, the cover 16 is slidably mounted to the housing 12 (FIG. 5), and the hinged actuation door 18 is rotated to a closed position (FIG. 6). Mounting the cover 16 to the housing 12 actuates the latching mechanism to release the platens 14 from their locked upper position and cause the platens 14 to drop onto the fluid-filled flexible containers 21 of the fluid delivery system. To activate the eye wash station, the actuation door 18 is rotated to the open position in FIG. 7. The construction and operation of the eye wash station 10 are described in detail below.

A top of the housing 12 is provided with a handle 25 for mounting the eye wash station 10 to a vertical wall or mobile cart in an industrial work station, laboratory, or other location where workers are exposed to gaseous fumes, liquids or solid materials which can irritate or injure eyes upon contact therewith (FIGS. 2–4). The vertical wall or mobile cart is preferably provided with a conventional J-hook (not shown) supporting the handle 25. The top wall of the cover 16 is preferably curved to discourage individuals from laying loose items on the cover 16 which could contaminate the eye wash station 10 (FIGS. 1, 5, 6, and 7).

The housing 12 supports the boxes 20 holding the respective flexible containers 21 and supports the nozzles 22 interconnected to the flexible containers 21 via the hoses 24 (FIG. 4). To support the boxes 20, the housing 12 forms a rigid shelf 26 of sufficient width and depth to accommodate the pair of boxes 20 in side-by-side relation to one another (FIGS. 1, 3, and 4). In addition to supporting the bottoms of the boxes 20, the housing 12 provides side walls 28 to support the outer sides of the boxes 20 and a vertical rear wall 30 to support the back sides of the boxes 20 (FIG. 4). The side walls 28 are preferably spaced from each other by a distance only slightly greater than the combined width of the boxes 20 so that the boxes 20 snugly fit between the side walls 28. By virtue of this snug fit, the inner sides of the boxes 20 abut each other so that the boxes 20 provide each other with mutual support.

Figure 17:
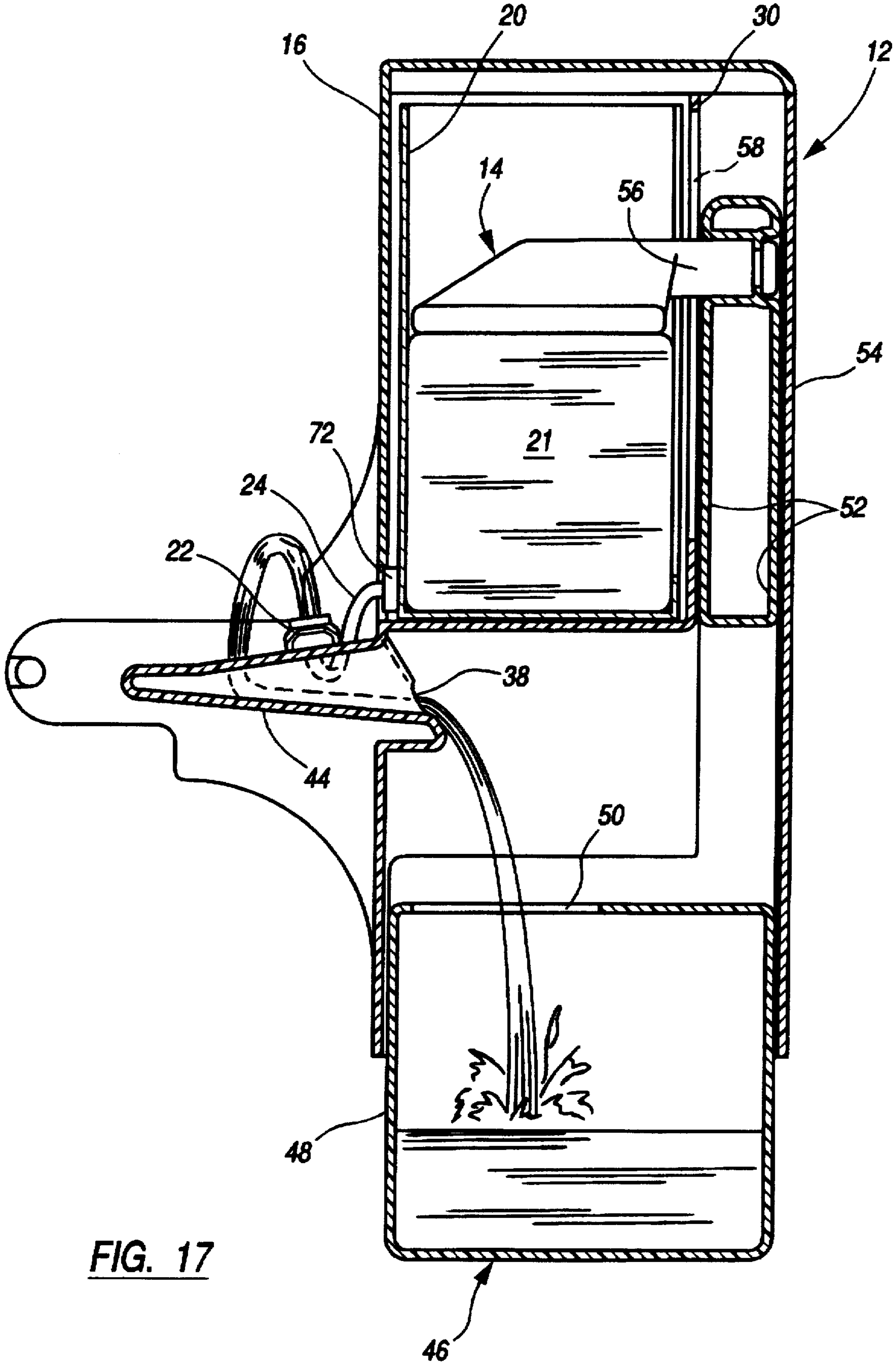
FIG. 17 is a cross-sectional view of the eye wash station, taken along a vertical plane passing through a nozzle of the eye wash station, showing eye wash fluid being dispensed from the nozzle and captured in a reservoir tank.

When the cover 16 is slidably mounted to the housing 12 as shown in FIGS. 6 and 7, the front wall of the cover 16 combines with the rear wall 30 (FIG. 4) of the housing 12 to support the respective front and back sides of the boxes 20. Referring to FIG. 17, the front wall of the cover 16 and the rear wall 30 of the housing 12 are preferably spaced from each other by a distance only slightly greater than the depth of the boxes 20 so that the boxes 20 snugly fit between the front wall of the cover 16 and the rear wall 30 of the housing 12. Thus, each of the boxes 20 is supported on its four vertical sides and its bottom. As will become apparent, this support is desired during operation of the eye wash station 10 to prevent bulging of the boxes 20 as the platens 14 press downward on the flexible containers 21 within the respective boxes 20. By supporting the sides of the boxes 20, the eye wash fluid in the flexible containers 21 is forced by the platen pressure out of the flexible containers 21 within the respective boxes 20 to the respective nozzles 22. In an alternative embodiment, the flexible containers 21 are loaded into the housing 12 without the surrounding boxes 20. To provide the loose containers 21 with support, the housing 12 includes a vertical front wall extending between the side walls 28. This front wall extends upwardly from the shelf 26 to the platens 14 when the platens 14 are in their upper position. Using this front wall, the housing 12 serves substantially the same support function as the boxes 20. The front wall may be hinged to the front edge of the shelf 26 to allow the front wall to be rotated downward to a horizontal position and permit front-loading of the flexible containers 21 into the housing 12. Alternatively, the platens 14 may be rotatable from their normal horizontal orientation to a vertical orientation to permit top-loading of the containers 21 into the housing 12.

To support the nozzles 22, the housing 12 includes a frontal nozzle mount 32 having a pair of elongated slots 34 formed therein (FIG. 1–3). These slots 34 cooperate with opposing grooves 36 (FIG. 8) formed in each nozzle 22 to slidably engage the nozzles 22 in the respective slots 34 (FIGS. 4, 5, and 7). This sliding engagement of the nozzles 22 in the respective slots 34 positively locates the nozzles 22 with respect to the housing 12. The width of each slot 34 is approximately the same as the width of each nozzle 22 in the region of the grooves 36 (FIG. 8) to create a fairly snug fit therebetween. To engage the nozzles 22 in the respective slots 34, the nozzles 22 are first positioned adjacent the outermost edges of the respective slots 34 (i.e., left edge of the left slot 34 and right edge of the right slot 34 in FIGS. 1–3). Next, with the opposing grooves 36 (FIG. 8) of each nozzle 22 aligned with the opposing elongated edges of each respective slot 34, the nozzles 22 are slid inwardly through the respective slots 34 with the opposing grooves 36 of each nozzle 22 slidably receiving the opposing elongated edges of each respective slot 34.

During the operation of the eye wash station 10, the nozzles 22 dispense the eye wash fluid contained in the respective flexible containers 21 within the boxes 20 (FIG. 18). The eye wash fluid dispensed from the nozzles 22 is captured in a basin 44 having a floor properly sloped to direct the eye wash fluid to a drain 38 (FIGS. 7 and 17). The drain 38 includes a pair of holes formed on opposite sides of the frontal nozzle mount 32. The eye wash fluid captured on the floor of the basin 44 flows backward around the nozzle mount 32 to the holes of the drain 38.

The eye wash fluid captured by the drain 38 is conveyed by the drain 38 to the reservoir 46. As best shown in FIGS. 1 and 17, the reservoir 46 includes a tank 48 of sufficient size to hold the volume of eye wash fluid contained in the flexible containers 21 within the boxes 20. The upper surface of the tank 48 forms a rectangular opening 50 to receive the eye wash fluid exiting the drain 38. The eye wash fluid flows through the holes of the drain 38 with sufficient velocity that the fluid is propelled into the rectangular opening 50 (FIG. 17). In an alternative embodiment, the drain 38 includes a pair of pipes extending from the respective drain holes to the rectangular opening 50 in the tank 48.

The bottom of the housing 12 is completely open to permit the tank 48 to extend upward into the housing 12 (FIGS. 2–7 and 17). When the tank 48 is empty prior to using the eye wash station 10, the housing 12 conceals a substantial portion of the tank 48 (FIG. 6). The tank 48 moves downward relative to the stationary housing 12 in response to the tank 48 collecting the eye wash fluid therein (FIG. 17). As more and more eye wash fluid enters the tank 48, the more the tank 48 is exposed beneath the housing 12. When the tank 48 is substantially filled with the eye wash fluid following use of the eye wash station 10, the tank 48 is substantially exposed (see FIG. 2). When the eye wash station 10 is mounted to a vertical wall or mobile cart in an industrial work station, laboratory, or the like, the eye wash station 10 is mounted at such a height that the tank 48 will not contact the floor or ground prior to being substantially filled with the eye wash fluid. The lower surface of the tank 48 is preferably curved to encourage proper mounting of the eye wash station 10 to a vertical wall. With this curved lower surface, the eye wash station 10 will not remain upright if it is allowed to stand freely on the floor or ground.

To stabilize the vertical movement of the tank 48 relative to the housing 12 so as to minimize lateral shifting of the tank 48 relative to the housing 12, the transverse cross-section of the tank 48 is substantially identical in shape to the transverse cross-section of the lowermost portion of the housing 12 (FIGS. 1–7). Moreover, the transverse cross-section of the tank 48 is only slightly smaller in size than the transverse cross-section of the lowermost portion of the housing 12. Thus, a tight tolerance exists between the housing 12 and the tank 48.

The reservoir 46 further includes a rear support 52 extending upward from a rear portion of the tank 48 (FIGS. 1 and 17). As best shown in FIG. 17, the rear support 52 extends into the housing 12 between the rear wall 30 and a second rear wall 54 parallel to the rear wall 30. The rear walls 30 and 54 define a narrow cavity in the housing 12 for receiving the rear support 52 of the reservoir 46. As the reservoir 46 moves vertically relative to the housing 12, the rear support 52 slides vertically through the cavity. To ensure smooth movement of the reservoir 46 relative to the housing 12, the width and thickness of the rear support 52 are only slightly smaller than the corresponding dimensions of the cavity. In accordance with the vertical movement of the tank 48, the rear support 52 slides vertically downward through the cavity as the tank 48 collects the eye wash fluid therein.

The platens 14 are mounted to the rear support 52 of the reservoir 46 by respective elongated members 56 (FIGS. 1 and 17). The elongated members 56 are connected to the rear support 52 by conventional means such as a quarter-turn lock. The platens 14 are vertically movable between an upper and lower position in response to corresponding vertical movement of the reservoir 46. To permit vertical movement of the platens 14, the rear wall 30 of the housing 12 is provided with a pair of vertical guide slots 58. The elongated members 56 extend from the interior of the housing 12, through the respective guide slots 58, and to the rear support 52 of the reservoir 46 (FIG. 17). Thus, as the platens 14 move between the upper and lower position, the elongated members 56 move vertically through the respective guide slots 58.

Figure 20:
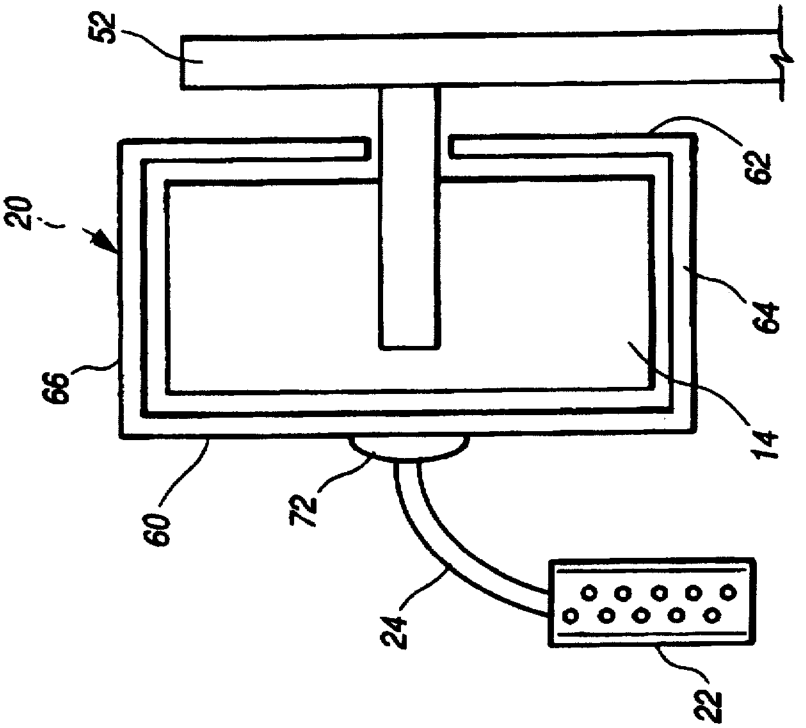
FIG. 20 is a top view of the fluid delivery system in FIG. 18 with a platen extending into the box and disposed about the flexible container within the box.

When the boxed flexible containers 21 are loaded into the housing 12, the platens 14 are located immediately above the flexible containers 21 (FIGS. 4, 17, and 20). As described below, the platens 14 are responsible for maintaining a constant flow of the eye wash fluid dispensed from the nozzles 22. The platens 14 press downward on the flexible containers 21 in the respective boxes 20 with a downward force proportional to a weight of the eye wash fluid collected in the reservoir 46. Therefore, the greater the volume of eye wash fluid in the reservoir 46, the greater the downward force that the platens 14 apply to the flexible containers 21.

More specifically, as the eye wash fluid from the flexible containers 21 is dispensed from the nozzles 22, captured by the drain 38, and collected in the tank 48 of the reservoir 46, the weight of this collected eye wash fluid is essentially transferred by the reservoir 46 to the platens 14 (FIG. 17). The reservoir 46 pulls downward on the platens 14 with a force approximately equal to the combination of the weight of the reservoir 46 and the weight of the collected eye wash fluid. Since the platens 14 are located immediately above the flexible containers 21 within the respective boxes 20, pulling downward on the platens 14 causes the platens 14 to press downward on the flexible containers 21 with a force equivalent to the aforementioned weight combination. This downward force maintains a constant flow of the eye wash fluid from the nozzles 22. Thus, the reservoir 46 and the platens 14 serve as a feedback mechanism using the weight of the collected eye wash fluid to apply downward force to the flexible containers 21.

Prior to using the eye wash station 10, the eye wash fluid delivery system is loaded into the housing 12. The delivery system includes a pair of identical delivery arrangements, one of which is best shown in FIG. 18. Each delivery arrangement includes the flexible container 21 within the box 20, the nozzle 22, and the flexible hose 24 interconnecting the nozzle 22 to the flexible container 21. Each of the foregoing components of the delivery arrangement is described in detail below.

Figure 19:
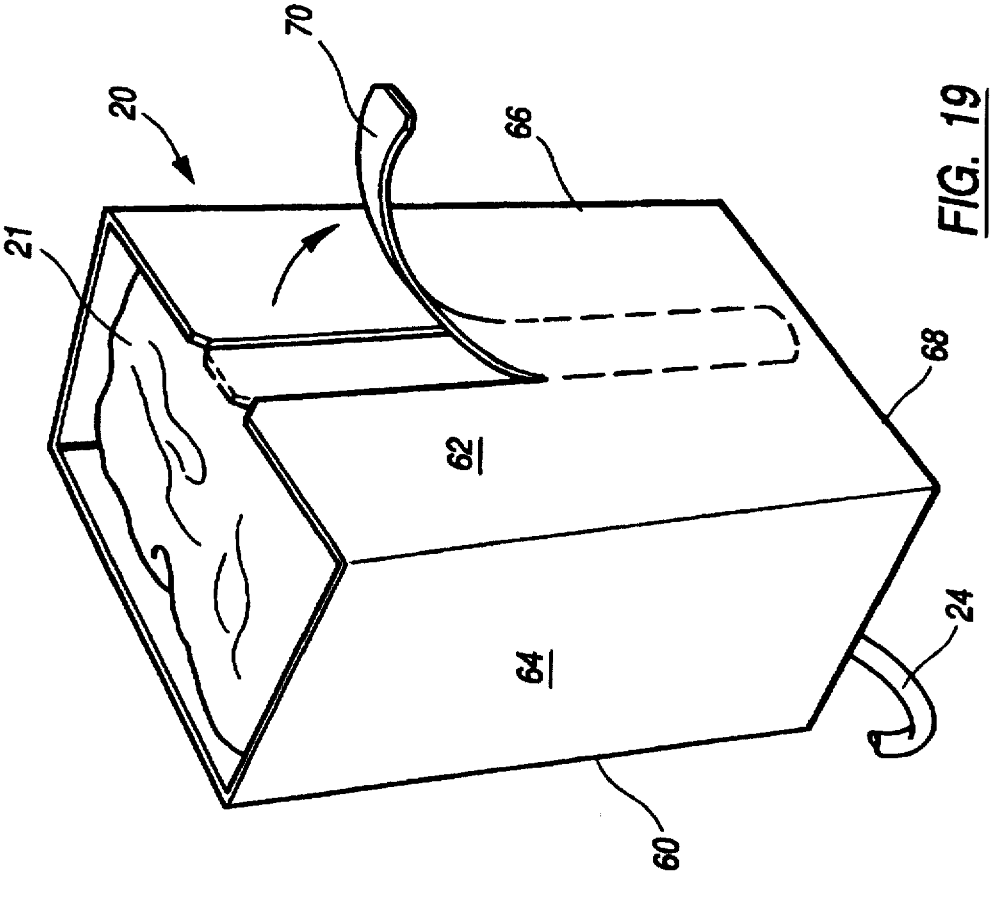
FIG. 19 is a perspective view of a boxed flexible container of the fluid delivery system in FIG. 18.

The box 20, shown in detail in FIGS. 18 and 19, contains the flexible container 21 substantially filled with eye wash fluid. The eye wash fluid is preferably a purified fluid such as a buffered isotonic saline solution, although it could be as simple as purified water. An exemplary solution is eyesaline® manufactured by Fendall Company of Arlington Heights, Ill. Alternatively, the purified eye wash fluid may have a special composition directed toward certain types of hazards. The flexible container 21 is preferably a metallized MYLAR™ bag including a layer of polyethylene. The box 20 is preferably composed of corrugated plastic or thick-walled corrugated paperboard. If the box 20 is composed of corrugated paperboard, the paperboard is preferably wax-coated to protect the box 20 against such environmental conditions as humidity. The box 20 includes opposing front and back walls 60 and 62, opposing side walls 64 and 66, and a bottom wall 68. To safeguard the flexible container within the box 20 during shipment thereof, the box 20 may also be provided with a temporary top wall (not shown). This top wall is removed prior to installation of the box 20 into the housing 12.

The back wall 62 of the box 20 includes a removable tear strip 70 extending downward from the upper edge thereof (FIG. 19). Like the top wall, the tear strip 70 safeguards the flexible container during shipment thereof and is removed prior to installation of the box 20 into the housing 12. Removing the tear strip 70 provides the back wall 62 of the box 20 with an elongated vertical clearance slot. This clearance slot is laterally positioned along the back wall 62 such that, following installation of the box 20 into the housing 12, the clearance slot is aligned with a respective one of the guide slots 58 formed in the rear wall 30 of the housing 12 (FIG. 4). When the elongated members 56 of the respective platens 14 extend through the respective guide slots 58, they also extend through the clearance slots in the back walls 62 of the respective boxes 20. As the elongated members 56 move vertically through the respective guide slots 58, they simultaneously move vertically through the clearance slots in the respective boxes 20.

The lower portion of the front wall 60 of the box 20 forms a hole sized to accommodate an outlet fitment 72 (FIG. 18). One end of the flexible hose 24 is firmly connected to this outlet fitment 72. The other end of the flexible hose 24 is firmly connected to an inlet fitment 74 on the nozzle 22. In the preferred embodiment, the hose 24 has an inner diameter of approximately 0.38 inches (0.95 cm).

Figure 14:
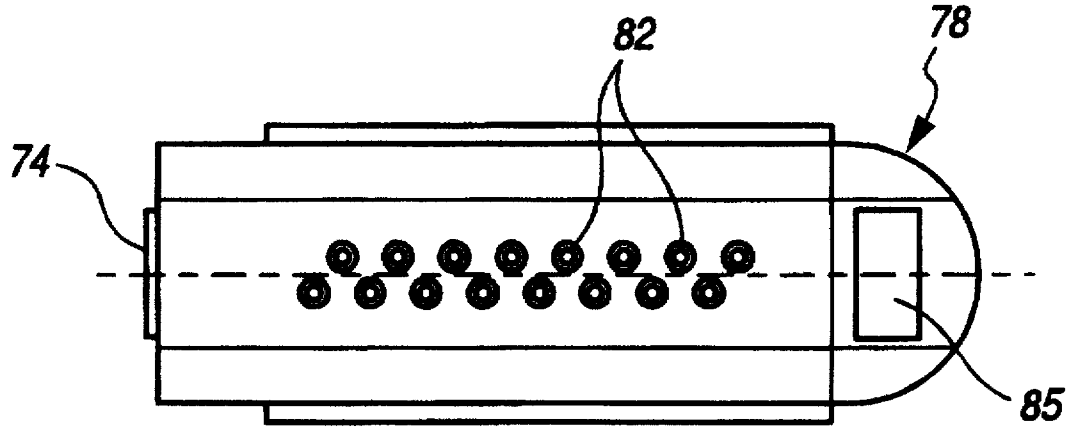
FIG. 14 is a top view of the lower nozzle body of the nozzle.
Figure 15:
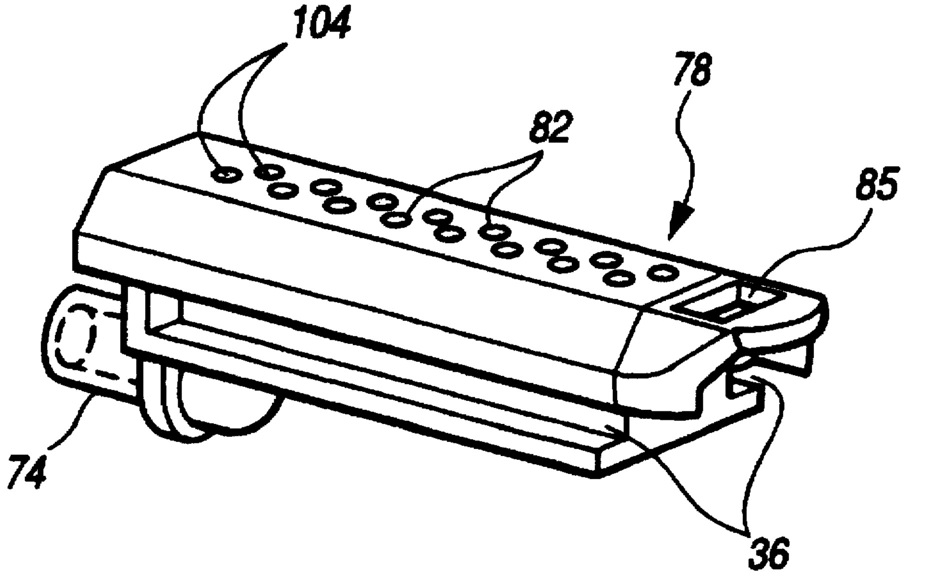
FIG. 15 is a perspective view of the lower nozzle body of the nozzle.

Referring now to FIGS. 8–15, each nozzle 22 includes an upper pressure plate 76 and a lower nozzle body 78. The lower nozzle body 78 includes the inlet 74, a distribution manifold 80 (FIG. 12), and an elongated array of apertures 82 (FIGS. 14 and 15). The distribution manifold 80, which receives eye wash fluid from the inlet 74, distributes the eye wash fluid to the apertures 82. The array of apertures 82 in the lower nozzle body 78 preferably includes approximately sixteen apertures arranged in two rows of eight apertures per row (FIGS. 14 and 15). To permit the nozzle 22 to be slidably mounted to the elongated slots 34 formed in the frontal nozzle mount 32 of the housing 12, the lower nozzle body 78 is provided with the opposing grooves 36.

Figure 8:
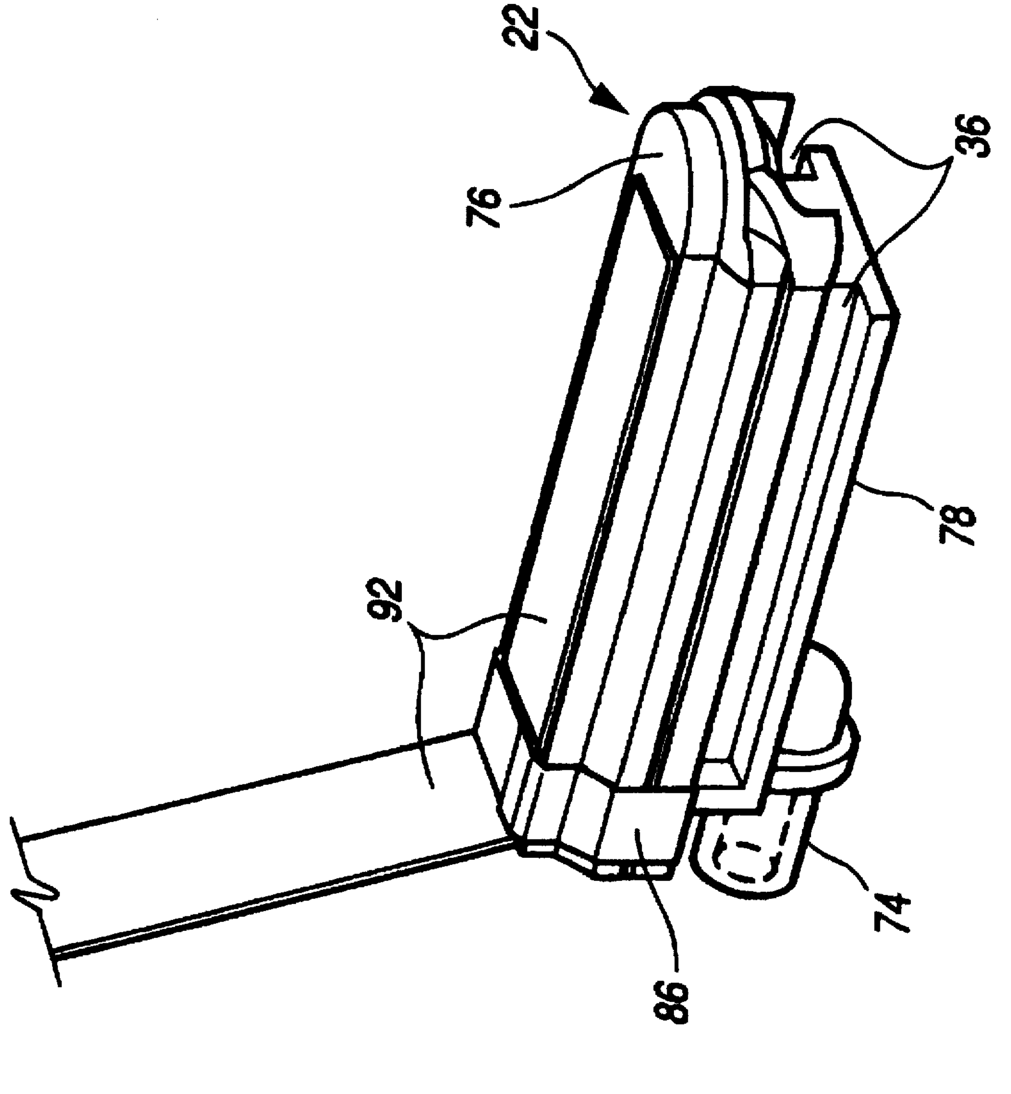
FIG. 8 is a perspective view of a nozzle of the eye wash station.
Figure 10:
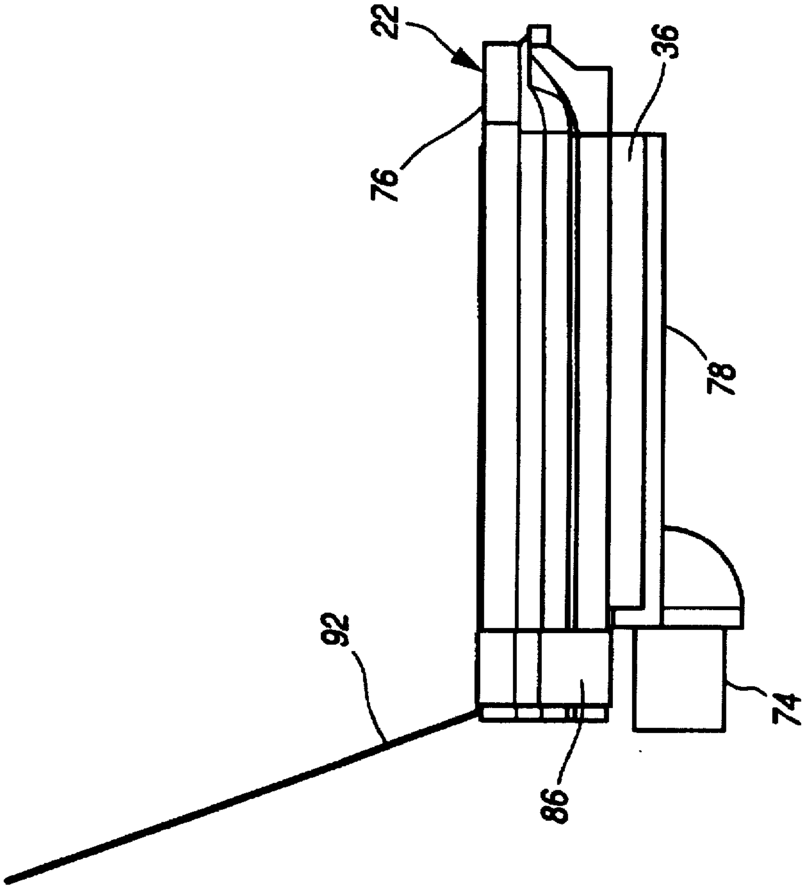
FIG. 10 is a side view of the nozzle in FIG. 8 prior to disengaging an upper pressure plate and a lower nozzle body of the nozzle.
Figure 12:
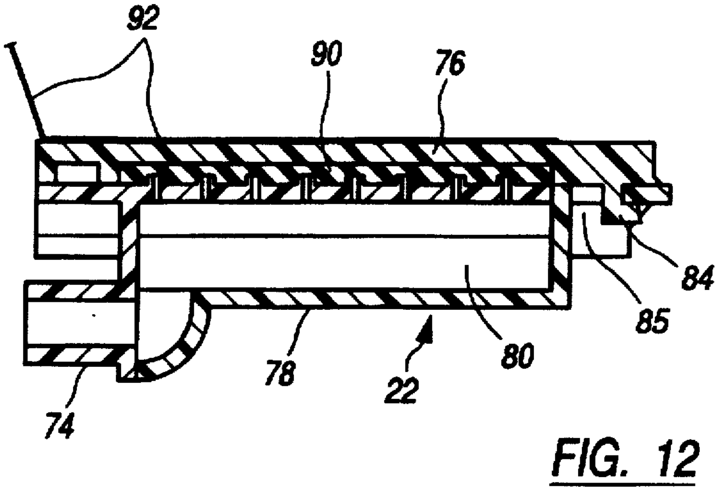
FIG. 12 is a cross-sectional view of the nozzle prior to disengaging the upper pressure plate and the lower nozzle body of the nozzle.
Figure 13:
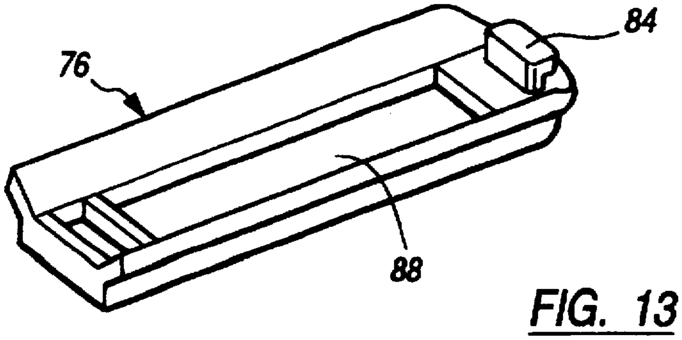
FIG. 13 is a perspective view of the upper pressure plate of the nozzle.

Prior to activation of the eye wash station 10, the upper pressure plate 76 is hingedly connected to the lower nozzle body 78. In particular, the upper pressure plate 76 forms a retaining tab 84 which is releasably held in a slot 85 formed in the lower nozzle body 78 (FIGS. 12–15). A seal element, such as a plastic shrink band 86, is used to firmly secure the upper pressure plate 76 to the lower nozzle body 78 such that the upper pressure plate 76 blocks the apertures 82 formed in the lower nozzle body 78 (FIGS. 8 and 10). The shrink band 86 tightly circumscribes the nozzle 22 at an opposite end of the nozzle 22 relative to the hinged connection of the pressure plate 76 and nozzle body 78. To hermetically seal the output ends of the apertures 82 prior to activation of the eye wash station 10, the upper pressure plate 76 forms an elongated pocket 88 (FIG. 13) which accommodates a rubber gasket 90 (FIG. 12). As best shown in FIG. 12, the gasket 90 presses against the apertures 82 to prevent air flow into the apertures and to prevent any possible leakage of the eye wash fluid therefrom.

To permit separation of the upper pressure plate 76 from the lower nozzle body 78, a flexible actuation strap 92, composed of a flexible polymeric material, woven fabric, or the like, is fixedly adhered or mechanically fastened to the upper surface of the upper pressure plate 76 (FIGS. 8, 9, 10, and 12). The strap 92 extends from the hinged end to the wrapped end of the upper pressure plate 76 or, alternatively, the strap 92 extends only from a middle portion of the upper pressure plate 75 to the wrapped end thereof. Moreover, the strap 92 passes beneath the shrink band 86 between the upper surface of the pressure plate 76 and the inner surface of the shrink band 86 (FIG. 8). The strap 92 is not adhered to the upper surface of the pressure plate 76 in the region beneath the shrink band 86. The manner in which this strap 92 is used to separate the upper pressure plate 76 from the lower nozzle body 78, and thereby permit eye wash fluid to be dispensed from the lower nozzle body 78 via the apertures 82, is described in detail below.

Until the eye wash station 10 is activated, the eye wash fluid delivery system is a hermetically sealed system extending from the flexible containers 21, through the respective hoses 24, to the nozzles 22 (FIGS. 4 and 18). This sealed delivery system prevents any contamination of the eye wash fluid passageway formed by the containers 21, the hoses 24, and the nozzles 22. The eye wash fluid in the sealed delivery system is not exposed to the environment. Moreover, the sealed delivery system maintains the stability of the eye wash fluid contained in that fluid passageway for a time period as long as approximately 2–3 years. Such long-term stability of the eye wash fluid is advantageous because if the eye wash station 10 goes unused, its unused delivery system need not be replaced with a new delivery system for 2–3 years. As a result, the maintenance required by the eye wash station 10 during long-term periods of nonuse is minimal.

To load the eye wash fluid delivery system into the housing 12, the cover 16 is slidably detached from the housing 12 so that the eye wash station 10 appears as in FIG. 2. Next, the pair of platens 14 are vertically moved to their upper position depicted in FIG. 3 if the platens 14 are not already in that upper position.

Figure 16A:
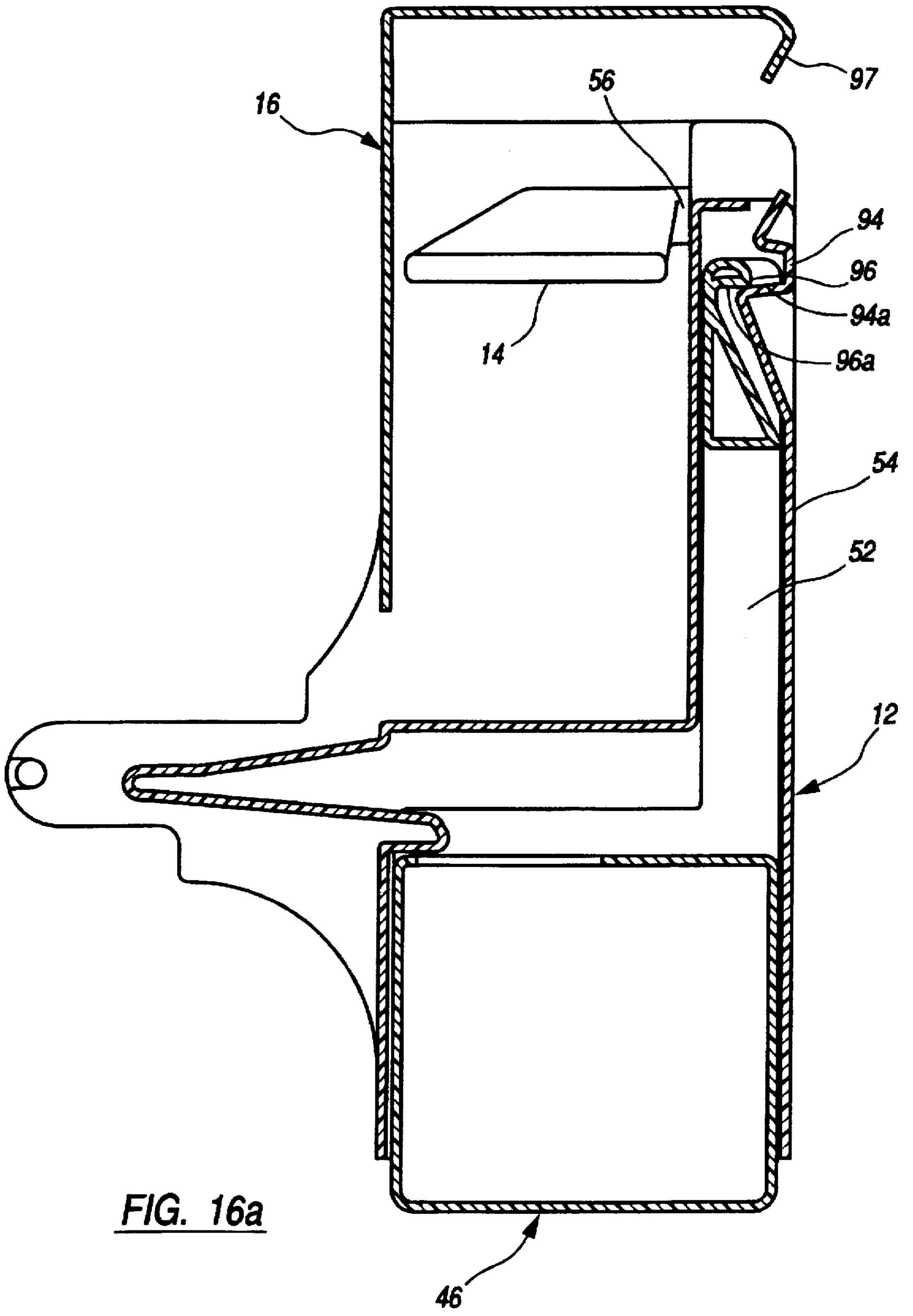
FIGS. 16*a–c* are cross-sectional views of the eye wash station, taken through a lower central portion of the eye wash station and then taken through an upper, laterally outward portion of the eye wash station, showing the cover in the process of being slidably mounted to a housing of the eye wash station.
Figure 16B:
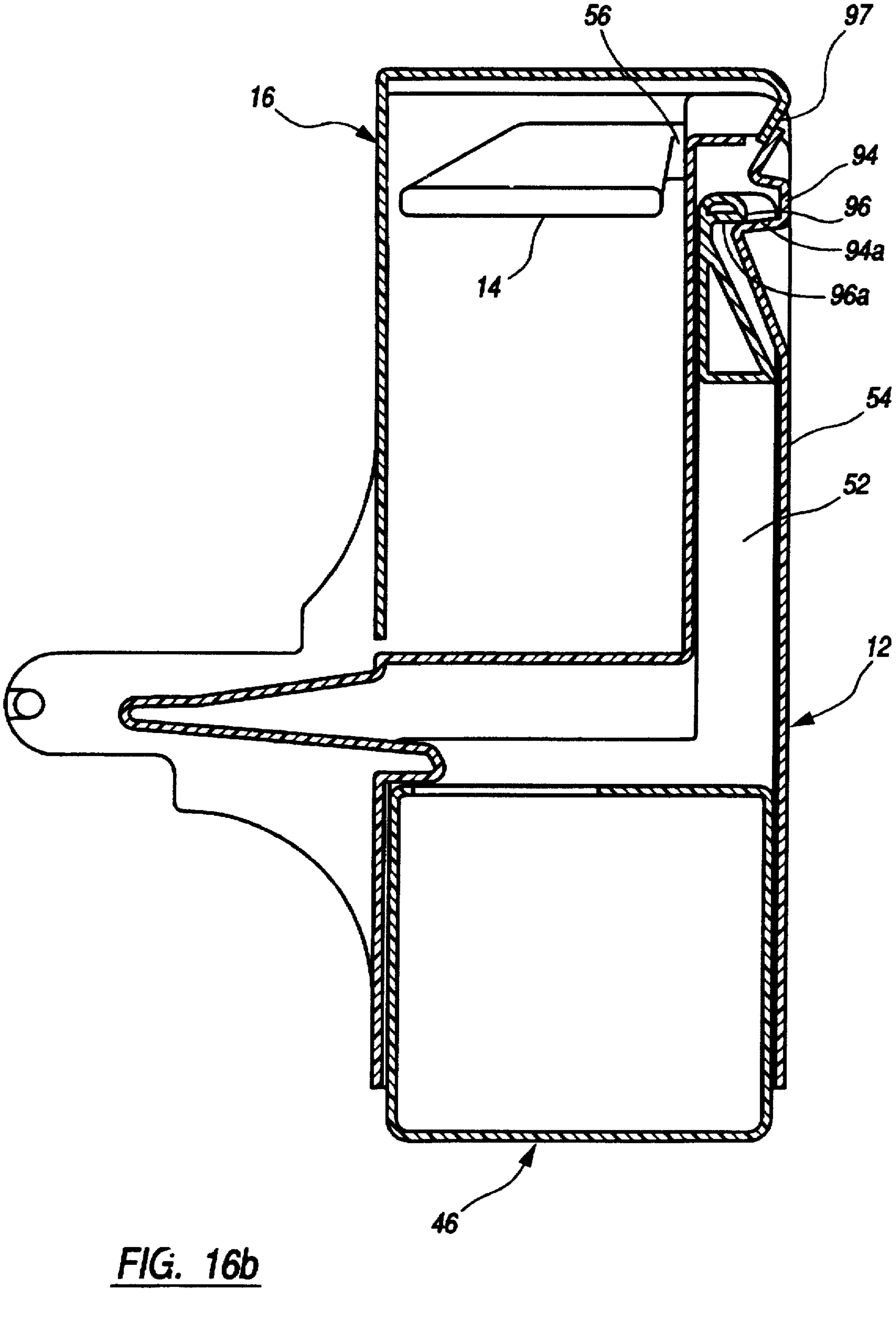
Figure 16C:
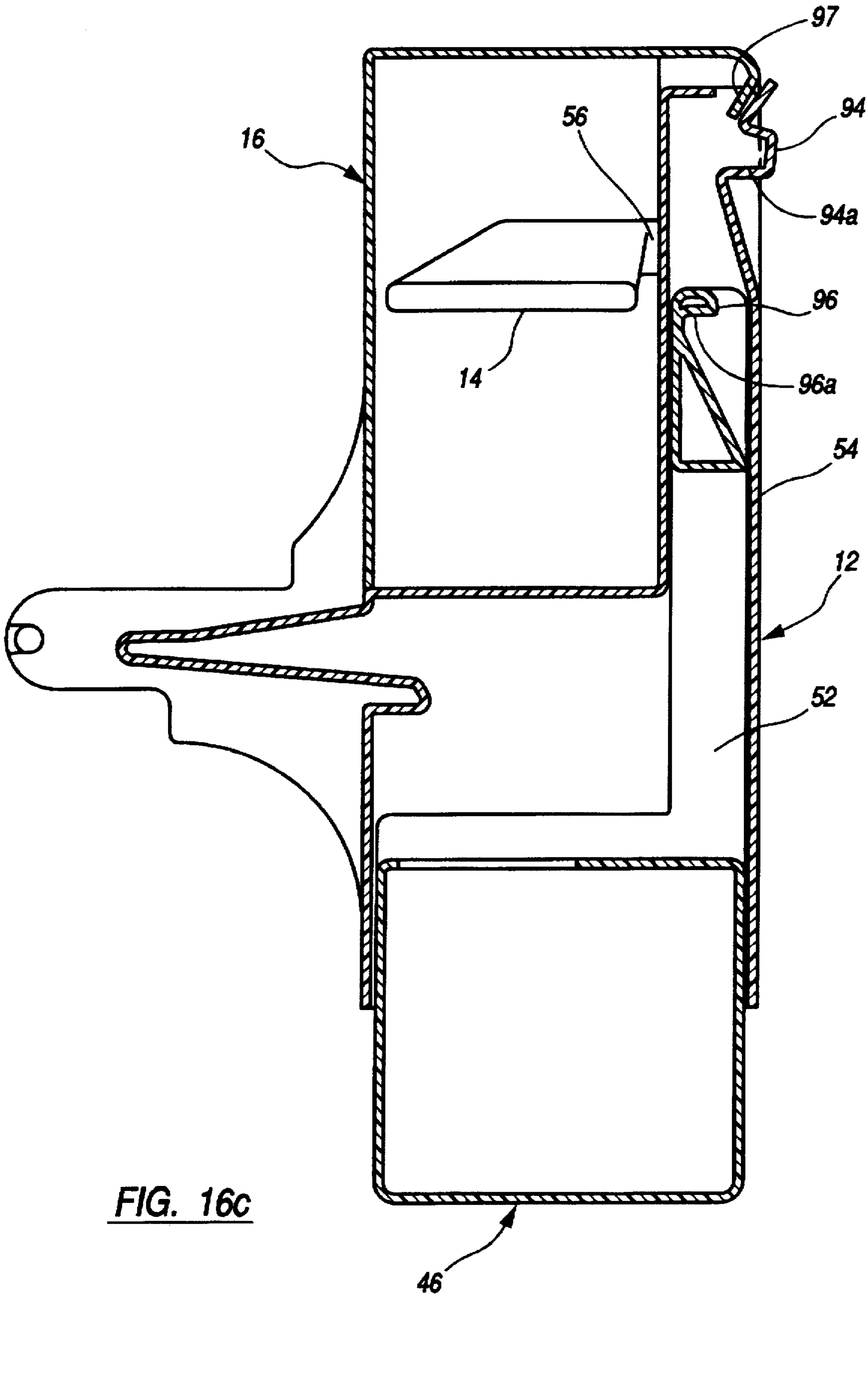

Referring now to FIGS. 1 and 16*a*–*c*, to maintain the platens 14 in the upper position without requiring an operator to hold the platens 14 in the upper position, a pair of platen-release latches 94 are formed by a deflectable outer upper portions of the outer rear wall 54 of the housing 12. The outer upper portions of the rear support 52 of the reservoir 46 form mating catches 96 (FIG. 1). FIGS. 16*a*–*c* are cross-sectional views of the eye wash station, taken through a lower central portion of the eye wash station and then jogging outward from this lower central portion to an upper, laterally outward portion of the eye wash station. This lower central portion is taken along a vertical plane of mirror symmetry passing through the center of the tank 48 and the centers of the respective basin 44 and nozzle mount 32 of the housing 12. The upper, laterally outward portion is taken along a vertical plane passing through one of the latches 94 and its associated catch 96.

When the platens 14 are moved to the upper position, each catch 96 serves as a cam which communicates motion to the associated latch 94, which serves as a cam follower. The catch 96 deflects the latch 94 clockwise (as viewed in FIGS. 16*a*–*c*) from its relaxed position until an edge 96*a* of the catch 96 advances beyond an edge 94*a* of the latch 94. At this point, the latch 94 springs back to its relaxed position with the edge 96*a* of the catch 96 engaging the edge 94*a* of the latch 94 (FIG. 16*a*). Since the platens 14 are mounted to the rear support 52 by the elongated members 56, engagement of the catches 96 by the respective latches 94 holds the platens 14 in their upper position.

With the platens 14 in their upper position, the boxes 20 holding the flexible containers 21 are placed within the housing 12 on the shelf 26 beneath the respective platens 14. Moreover, the nozzles 22 are mounted to the frontal nozzle mount 32 by slidably engaging the grooves 36 formed in the lower nozzle body 78 of each nozzle 22 with the respective slots 34 formed in the nozzle mount 32.

After installing both the boxes 20 and the nozzles 22 into the housing 12, the cover 16 is slidably mounted to the housing 12 (FIG. 5). The housing 12 preferably forms a vertical track for receiving the sliding cover 16. The cover 16 and the housing 12 form respective engaging portions, such as mating male and female nubs, for holding the cover 16 in the closed position. While closing the cover 16, the hoses 24 are fed through respective hose clearance notches 40 formed in the lower edge of the cover 16.

Referring to FIGS. 16*a*–*c*, the cover 16 is preferably designed to automatically disengage each platen-release latch 94 from the associated catch 96 upon closure thereof. The cover 16 forms a downwardly-extending rear tab 97. Mounting the cover 16 to the housing 12 causes the tab 97 to deflect the latch 94 clockwise until the edge 94*a* of the latch 94 no longer supports the edge 96*a* of the catch 96, thereby releasing the rear support 52 (FIG. 16*c*). Since the platens 14 are connected to the rear support 52, disengaging the rear support 52 releases the platens 14 from their upper position so that the platens 14 drop onto the flexible containers 21 within the respective boxes 20 (FIG. 4). The boxes 20 are sized to accommodate the respective platens 14 therein while providing minimal space between the peripheries of the platens 14 and the vertical walls 60, 62, 64, and 66 of the respective boxes 20. In an alternative embodiment, buttons are mounted to the housing 12 and coupled to the respective latches 94. Prior to mounting the cover 16 to the housing 12, the buttons are depressed to disengage the latches 94 from the respective catches 96.

After mounting the cover 16 to the housing 12, the straps 92 are laid out to the sides (FIG. 5). Next, the actuation door 18 is rotated to its closed position (FIG. 6). While closing the actuation door 18, the straps 92 are pulled about opposing sides of the actuation door 18. The opposing sides of the actuation door 18 form locating notches 100 for receiving the respective straps 92 (FIGS. 5 and 6). With the actuation door 18 closed and the straps 92 passing through the respective notches 100, the loose ends of the straps 92 are fastened to the actuation door 18 by detachable fastening means. In one embodiment, the detachable fastening means includes male fasteners 101 attached to the ends of the straps 96 and holes 103 formed in the actuation door 18 slightly inward from the notches 100. The male fasteners 101 form barbs to firmly secure these fasteners within the respective holes 103. The length of the straps 92 is selected such that the straps 92 are sufficiently slack to avoid placing undue stress on the shrink bands 86, and yet are sufficiently taut to fit within the notches 100 formed in the opposing sides of the door 18 so that slippage is not a problem when the eye wash station 10 is activated. The eye wash station 10 is now ready for operation in the event of an emergency requiring a user to flush his or her eyes. Prior to such an emergency, the actuation door 18 serves as a dust cover protecting the nozzles 22 and basin 44 from contaminants in the environment.

Figure 9:
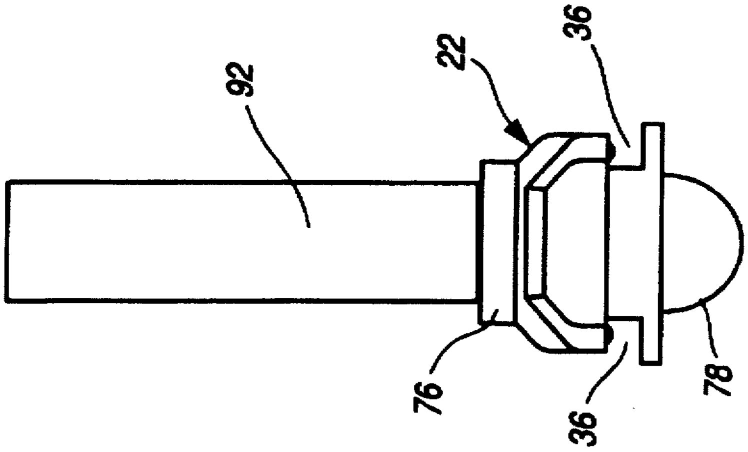
FIG. 9 is an end view of the nozzle in FIG. 8.
Figure 11:
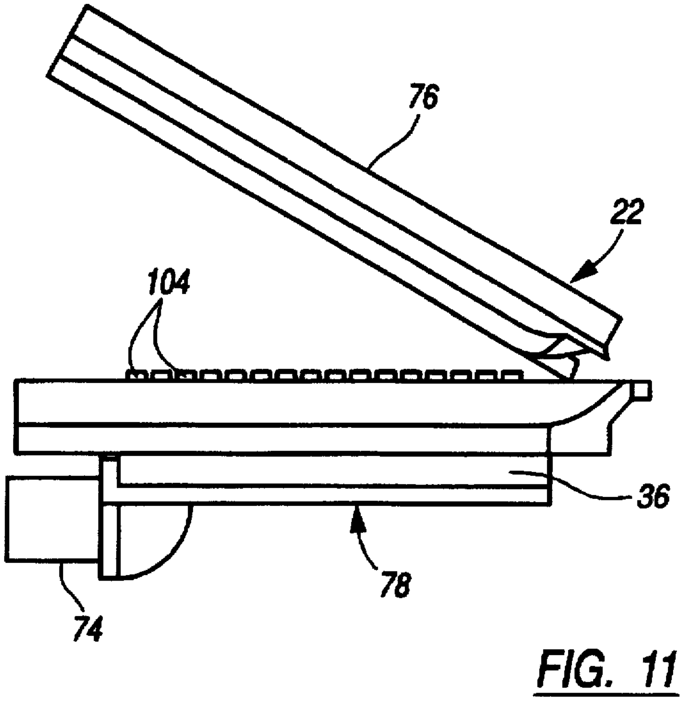
FIG. 11 is a side view of the nozzle with the upper pressure plate and the lower nozzle body of the nozzle in the process of being disengaged from each other.

In response to an emergency requiring immediate eye flushing, the user opens the actuation door 18 by grasping onto its integrally-formed handle 102 and pulling the actuation door 18 via the handle 102 to its open position (FIG. 7). Opening the actuation door 18 activates the flow of the eye wash fluid from the nozzles 22 by pulling the straps 92 relative to the respective nozzles 22. More specifically, opening the actuation door 18 pulls each strap 92 in a direction countering the force applied by the associated shrink band 86 to the nozzle 22 (FIGS. 8–10). Pulling the actuation strap 92 first breaks the shrink band 86, and continued pulling of the strap 92 rotates the pressure plate 76 upward about the hinged connection between the pressure plate 76 and the nozzle body 78 (FIG. 11). As the actuation door 18 reaches its open position (FIG. 7), the retaining tab 84 (FIG. 13) of each upper pressure plate 76 is dislodged from its slot 85 (FIG. 15) in the associated lower nozzle body 78 to completely separate the pressure plate 76 from the nozzle body 78.

When the actuation door 18 is in its open position, the pressure plates 76 hang from the actuation door 18 by virtue of their attachment to the straps 92 which, in turn, are fastened to the actuation door 18 (FIG. 7). The lower nozzle bodies 78 of the respective nozzles 22 remain engaged in the slots 34 formed in the frontal nozzle mount 32 of the housing 12.

With the pressure plates 76 separated from their respective lower nozzle bodies 78, the eye wash fluid from the flexible containers 21 is dispensed from the lower nozzle bodies 78 via the apertures 82 (FIG. 15). Each aperture 82 provides a separate stream of eye wash fluid. The user flushes his or her eyes by bending over and positioning his or her eyes over the dispensed streams of eye wash fluid. The left eye is flushed with the streams emitted from the left nozzle body, while the right eye is flushed with the streams emitted from the right nozzle body. While flushing his or her eyes, the user typically leans on the eye wash station 10 for balance and support by placing his or her elbows on right and left arms 105*a*, 105*b* (FIG. 7) of the housing 12. The user holds his or her eyes open with his or her fingers to permit flushing thereof.

To prevent the emitted streams from falling back on the apertures 82 in the nozzle bodies 78, the streams are emitted from the lower nozzle bodies 78 at a slight forward angle relative to the vertical direction (FIG. 17). In the preferred embodiment, this angle is approximately eight degrees relative to the vertical direction. Moreover, to minimize wicking between the multiple streams dispensed from each nozzle body 78, the upper surface of each nozzle body 78 forms an array of nipples or standoffs 104 (FIGS. 11 and 15). The apertures 82 extend through the respective nipples 104 so that the streams are emitted from the lower nozzles bodies 78 via the nipples 104. In the preferred embodiment, the nipples 104 extend approximately 0.063 inches (1.6 mm) above the flat portion of the upper surface of the associated nozzle body 78. Since the apertures 82 are arranged in an elongated array (FIGS. 14 and 15), the streams of eye wash fluid emitted from each nozzle body 78 form an elongated ribbon-like pattern. It has been found that this elongated pattern provides better coverage to the eyes of the user than nozzles having apertures arranged in a circular array.

As described previously, the eye wash fluid dispensed from the nozzles 22 is captured by the drain 38 which, in turn, directs the captured eye wash fluid to the opening 50 in the tank 48 of the reservoir 46 (FIG. 17). As the eye wash fluid is collected in the tank 48, the weight of the collected eye wash fluid is transferred to the platens 14 via the rear support 52 of the reservoir 46. The platens 14 apply a downward force to the respective flexible containers 21 proportional to the weight of the eye wash fluid collected in the tank 48. Since the volume of the collected eye wash fluid steadily increases over time, the weight of the collected eye wash fluid steadily increases over time and the downward force applied by the platens 14 to the respective flexible containers 21 steadily (linearly) increases over time. This downward force keeps the height of the fluid spray pattern and the flow of the eye wash fluid dispensed from the nozzles 22 constant over time until minimal fluid remains in the flexible containers 21.

The flexible containers 21 contain a sufficient volume of the eye wash fluid so that the nozzles 22 deliver no less than 0.4 gallons per minute (1.5 liters per minute) of eye wash fluid for a time period of 15 minutes. In the preferred embodiment, the fluid flow rate is approximately 0.45 gallons per minute, and the flow rate does not fluctuate from this value until the flexible containers 21 substantially run out of the eye wash fluid. The eye wash station 10, including the size of the flexible containers 21 and the pressure applied by the platens 14, can be modified to achieve a different flow rate for a different time period in order to satisfy any changes in the standards for eye wash stations.

As the eye wash fluid is dispensed from the flexible containers 21, the platens 14 move vertically downward from their upper position toward their lower position. When substantially all the eye wash fluid has been dispensed from the flexible containers 21, the platens 14 are in their lower position and the emergency use of the eye wash station 10 has been completed.

To prepare the eye wash station 10 for another potential emergency, service personnel discard the waste fluid collected in the tank 48, discard the used eye wash fluid delivery system, and load a fresh eye wash fluid delivery system into the housing 12. To remind the service personnel that the used eye wash station 10 is in need of servicing, the tank 48 is preferably printed with such language as "UNIT DISCHARGED" or "UNIT DISCHARGED—SERVICE IMMEDIATELY" (FIGS. 1 and 2). This language is hidden by the housing 12 prior to use of the station 10 (FIG. 6), but is exposed following use of the station 10.

To discard the waste fluid collected in the tank 48, the tank 48 is provided with an integral valve 106 at its lower end for draining the waste fluid from the tank 48 into a conventional waste container positioned beneath the tank 48 (FIGS. 1–7). Opening the valve 106 permits the waste fluid to empty into the waste container. To prevent the service personnel from forgetting to close the valve 106 after emptying the waste fluid from the tank 48, the valve 106 may be a self-closing valve. If the valve 106 is self-closing, the service personnel must hold the valve 106 while draining the waste fluid from the tank 48. Alternatively, the valve 106 may be designed with a lever which only permits the tank 48 to be lifted upward into the housing 12 when the lever is in the closed position. When the valve 106 is in the open position, the lever interferes with the housing 12 when the service personnel attempt to raise the tank 48 upward into the housing 12. When the valve 106 is in the closed position, the lever clears the housing 12 when the tank 48 is lifted upward.

To discard the used eye wash fluid delivery system, the cover 16 is slidably removed from the housing 12 to permit access to the interior of the housing 12. Next, the tank 48 is lifted upward into the housing 12 until the latches 94 engage the respective catches 96 in the rear support 52. Since the tank 48 is connected to the platens 14 via the rear support 52, lifting the tank 48 effectively moves the platens 14 from their lower position to their upper position. Engagement of the catches 96 by the respective latches 94 maintains the platens 14 in their upper position. The lower nozzle bodies 78 of the nozzles 22 are then slidably disengaged from their respective slots 34, and the straps 92 are disconnected from the actuation door 18 to detach the upper pressure plates 76 of the nozzles 22 from the door 18. After detaching the engageable components of the used delivery system from the housing 12, all the components of the used delivery system, including the boxes 20, the substantially empty flexible containers 21, the hoses 24, the upper pressure plates 76, the lower nozzle bodies 78, and the straps 92, are discarded.

After discarding the used delivery system, a fresh (unused) eye wash fluid delivery system is loaded into the housing 12 (FIGS. 4–6). Since the procedure for loading the delivery system into the housing 12 is described above, it will not be repeated in detail herein. It suffices to state that new boxes 20 holding new flexible containers 21 containing fresh eye wash fluid are placed within the housing 12 on the shelf 26 beneath the respective platens 14, and new nozzles 22 are slidably mounted to the frontal nozzle mount 32. Next, the cover 16 is mounted to the housing 12 to disengage the latches 94 from the respective catches 96 and cause the platens 14 to drop onto the new flexible containers 21. Finally, the actuation door 18 is closed, and new straps 92 extending from the new nozzles 22 are fastened to the actuation door 18. The eye wash station 10 is now ready for emergency use.

The eye wash station 10 is manufactured using conventional plastic molding techniques. For example, the housing 12, the platens 14, the cover 16, and the actuation door 18 are composed of plastic and are manufactured using conventional rotational molding or blow molding techniques. The nozzles 22 are composed of molded plastic and are manufactured using conventional injection molding techniques. The straps 92 are preferably labelled with a batch identification number and an expiration date to provide a means for informing the user of the freshness of the eye wash fluid in the flexible containers 21.

While the present invention has been described with reference to one or more particular embodiments, those skilled in the art will recognize that many changes may be made thereto without departing from the spirit and scope of the present invention.

For example, the pair of platens 14 may be replaced with a single large platen attached to the rear support 52 of the reservoir 46 by one or more elongated members akin to the elongated members 56. These elongated members extend through corresponding vertical slots formed in the rear wall 30 of the housing 12, where the vertical slots permit vertical movement of the elongated members relative to the housing 12. In this embodiment, the pair of boxes 20 containing the respective flexible containers 21 are replaced with a single box containing a single flexible container. If a single flexible container is employed, the pair of nozzles 22 may be replaced with a single elongated nozzle slidably mounted to a single elongated slot formed in the frontal nozzle mount 32 of the housing 12. This single nozzle is interconnected to the single flexible container by a single flexible hose.

Figure 21A:
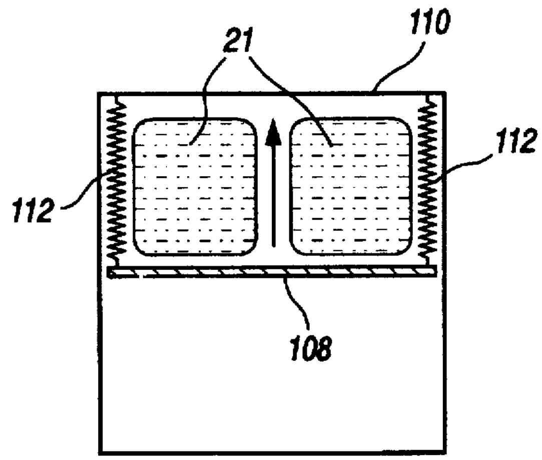
FIGS. 21*a–d* are schematic views showing various pressure application techniques for maintaining a constant fluid flow rate in an eye wash station in accordance with the present invention.
Figure 21B:
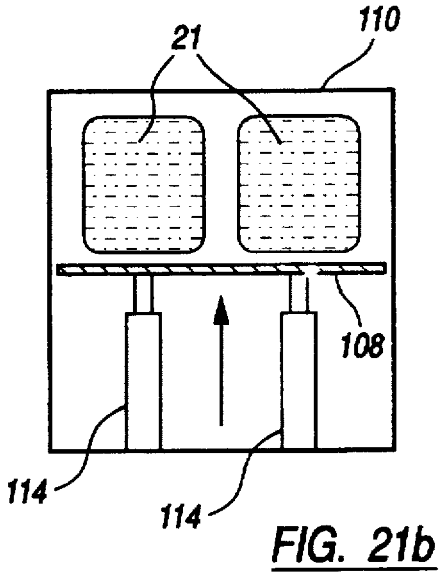
Figure 21C:
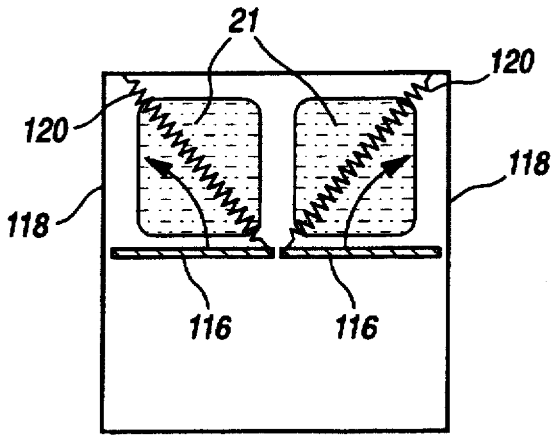
Figure 21D:
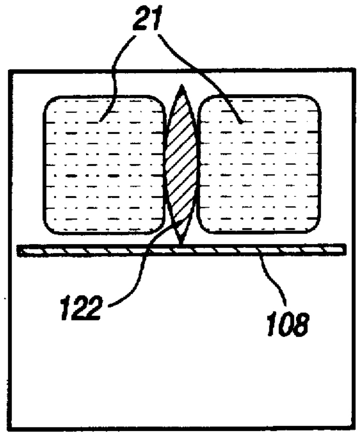

Furthermore, other pressure application techniques may be used to maintain pressure on the flexible containers 21 and thereby maintain a constant flow of the eye wash fluid dispensed from the nozzles 22. FIG. 21*a*, for example, schematically depicts a spring-lifted support method where the flexible containers 21 are raised as the eye wash fluid is dispensed therefrom. The flexible containers 21 sit on a movable shelf 108 hanging from a stationary top wall 110 by extension springs 112. The springs 112 force the shelf 108 upward, and the shelf 108, in turn, presses the flexible containers 21 against the stationary top wall 110. Raising the shelf 108 upward as the fluid is dispensed from the flexible containers 21 maintains the head height of the fluid at its initial level relative to the nozzles, thereby maintaining a constant fluid flow rate. FIG. 21*b* schematically depicts a gas cylinder-lifted support method where the extension springs 112 in FIG. 21*a* are replaced with gas cylinders 114 which force the shelf 108 upward so that the shelf 108 presses the flexible containers 21 against the stationary top wall 110. Once again, the fluid head height is maintained at a constant level relative to the nozzles. FIG. 21*c* schematically depicts a spring-lifted hinged shelf method where the flexible containers 21 sit on respective shelves 116 hingeally connected to respective opposing side walls 118. The hinges are designed to prevent the shelves 116 from rotating below the horizontal position in FIG. 21*c*. The inner edges of the shelves 116 are attached to the respective side walls 118 by respective extension springs 120. As the eye wash fluid drains from the flexible containers 21, the springs 120 rotate the shelves 116 in the direction of the arrows so that the shelves 116 press the flexible containers 21 against the top wall 110 and the respective side walls 118. FIG. 21*d* schematically depicts a $CO_2$ bladder method where a bladder 122 is positioned between the flexible containers 21 sitting on the stationary shelf 108. The bladder 122 slowly expands to maintain pressure on the flexible containers 21 as the eye wash fluid is drained therefrom.

Figure 22:
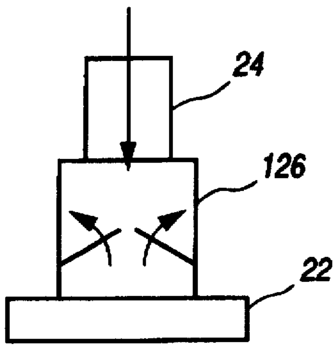
FIG. 22 is a schematic view of a deformable flow restrictor, connected to a nozzle of an eye wash station, for maintaining a constant fluid flow rate in the eye wash station.

Yet another technique for maintaining a constant fluid flow rate is schematically illustrated in FIG. 22. In this technique, pressure is not applied to the flexible containers 21. Rather, a deformable flow restrictor 126 is connected in the fluid flow path between each flexible container 21 and the associated nozzle 22. For example, as depicted in FIG. 22, the deformable flow restrictor 126 may be connected to the nozzle 22, and the hose 24 may, in turn, be connected to an input end of the deformable flow restrictor 126. To maintain a constant fluid flow rate as the fluid pressure decreases, the deformable flow restrictor 126 contains a flexible valve which gradually deforms (opens) as indicated by the arrows in FIG. 22.

Figure 23:
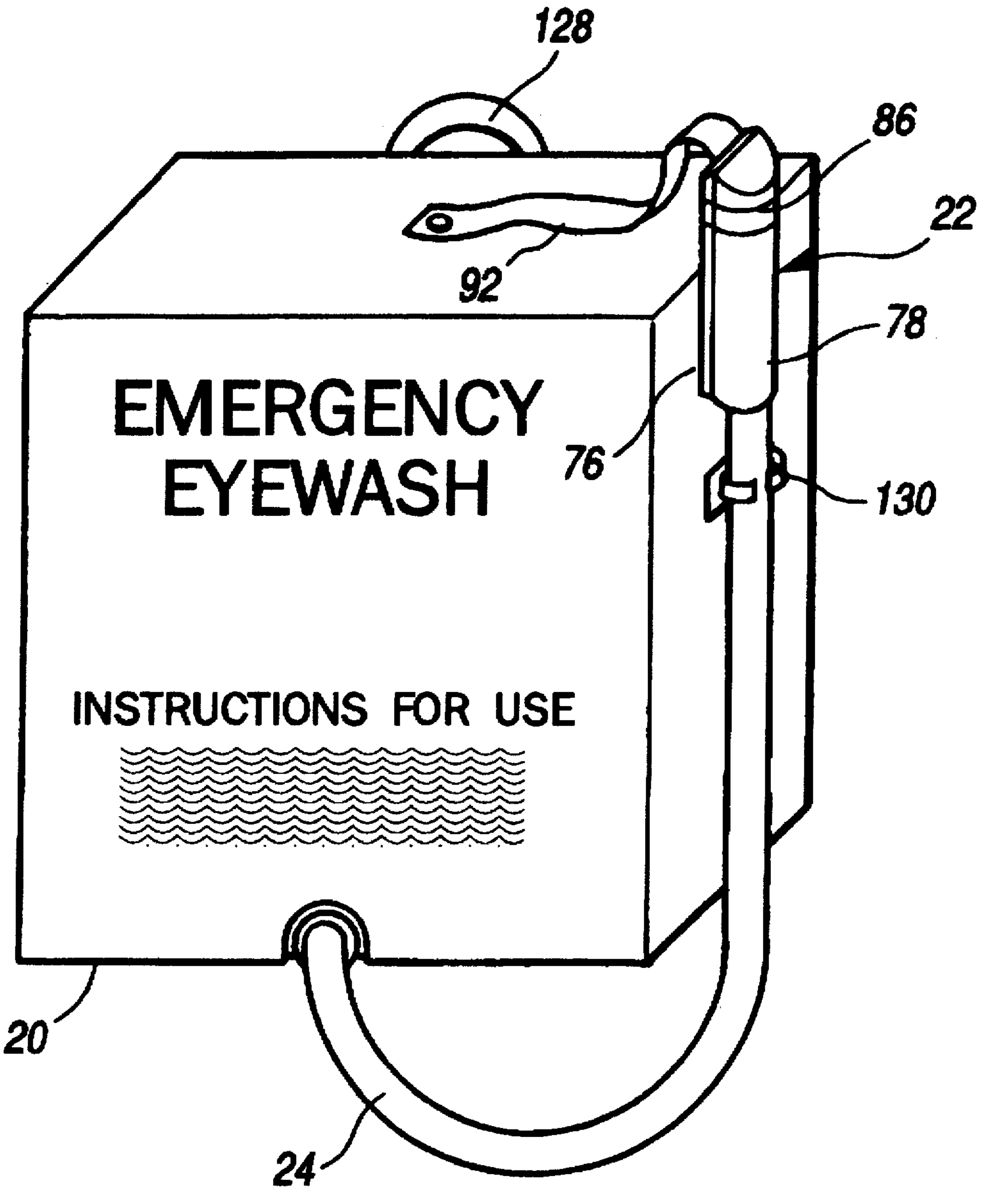
FIG. 23 is a perspective view of a self-contained fluid delivery system used as a stand alone eye wash station.

In a further alternative embodiment, the self-contained delivery system depicted in FIG. 23 may be used as a stand alone eye wash system. As illustrated in FIG. 23, in such a stand alone system, the box 20 holding a fluid-filled flexible container is hung on a wall or in a vehicle using a hanging strap 128. The nozzle 22 is mounted to the box 20 using a retainer clip 130. The actuation strap 92 is affixed to the box by adhesive or the like. When the stand alone system is needed, the user grabs onto the nozzle 22 or hose 24 and pulls, thereby breaking the seal band 86 and detaching the pressure plate 76 from the lower nozzle body 78. The user holds the lower nozzle body 78 in one hand while rinsing his or her eye(s). It should be understood that the stand alone system in FIG. 23 is preferably employed as a secondary eye wash station which would allow the user to quickly flush his or her eyes until he or she has access to a primary eye wash station, such as the eye wash station in FIG. 6. An advantage of the stand alone system in FIG. 23 is that it can be readily carried in a vehicle or to a remote site.

To permit the eye wash station 10 to be used in cold-temperature environments, the eye wash station 10 may be provided with heating elements to maintain the eye wash fluid in a comfortable temperature range (70°–80° F.) and prevent freezing thereof. These heating elements may be plate heaters arranged to heat the entire interior of the eye wash station 10 so that the nozzles 22, the hoses 24, and the flexible containers 21 are kept warm. Additionally, an insulating jacket with a movable flap (for activation) may cover the exterior of the eye wash station 10.

Each of these embodiments and obvious variations thereof is contemplated as falling within the spirit and scope of the claimed invention, which is set forth in the following claims.

What is claimed is:

1. An eye wash fluid delivery system, comprising:

a flexible container containing an eye wash fluid;

a nozzle in fluid communication with said container, said nozzle including an upper pressure plate and a lower nozzle body, said lower nozzle body forming an inlet for receiving the eye wash fluid from the container and forming a plurality of apertures in fluid communication with said inlet, said upper pressure plate being detachably linked to said lower nozzle body;

a seal element removably coupled to said nozzle, said seal element firmly securing said upper pressure plate to said lower nozzle body such that said upper pressure plate blocks said apertures formed in said lower nozzle body; and an actuation element, coupled to said seal element, for removing said seal element from said nozzle.

2. The delivery system of claim 1, wherein said actuation element includes an actuation strap fixedly attached to said upper pressure plate, and wherein said seal element is removed from said nozzle in response to pulling said actuation strap relative to said seal element.

3. The delivery system of claim 2, wherein said seal element includes a shrink band encircling said upper pressure plate and said lower nozzle body, and wherein said actuation strap extends between said shrink band and said upper pressure plate such that pulling said actuation strap relative to said shrink band breaks said shrink band.

4. The delivery system of claim 1, further including a semi-rigid box containing said flexible container.

5. The delivery system of claim 4, wherein said semi-rigid box includes a removable tear strip along a side wall thereof to form an elongated slot in said side wall.

6. The delivery system of claim 1, wherein said flexible container includes an outlet, and further including a flexible hose having first and second ends, said first end of said hose being connected to said outlet of said container, said second end of said hose being connected to said inlet of said lower nozzle body.

7. The delivery system of claim 1, wherein said upper pressure plate includes a gasket blocking said apertures formed in said lower nozzle body.

8. The delivery system of claim 1, wherein said lower nozzle body includes nipples and said apertures extend through respective ones of said nipples.

9. The delivery system of claim 1, wherein said lower nozzle body forms a pair of opposing mounting grooves for mounting said lower nozzle body to a slot formed in a nozzle support.

10. An eye wash fluid delivery system, comprising:

a flexible container containing an eye wash fluid and including an outlet;

a nozzle forming an inlet for receiving the eye wash fluid from the container and forming a plurality of apertures in fluid communication with said inlet, said nozzle being switchable from an initial sealed condition blocking said apertures to an open condition exposing said apertures, said nozzle being disposed external to said flexible container when said nozzle is in said initial sealed condition; and an elongated flexible hose extending from said outlet of said flexible container to said inlet of said nozzle.

11. An eye wash fluid delivery system, comprising:

a flexible container containing an eye wash fluid and including an outlet;

a nozzle forming an inlet for receiving the eye wash fluid from the container and forming a plurality of apertures in fluid communication with said inlet, said nozzle being switchable from an initial sealed condition blocking said apertures to an oven condition exposing said apertures, said nozzle a pair of opposing mounting grooves slidably mountable to a slot formed in a nozzle support; and a flexible hole extending from said outlet of said flexible container to said inlet of said nozzles.

12. The delivery system of claim 10, further including a seal element removably coupled to said nozzle, said seal element firmly maintaining said nozzle in said initial sealed condition, and further including a seal-breaking element coupled to said seal element for breaking said seal element and switching said nozzle to said open condition.

* * * * *